United States Patent
Diwu et al.

(12) 
(10) Patent No.: US 6,329,205 B1
(45) Date of Patent: Dec. 11, 2001

(54) DETECTION METHOD USING LUMINESCENT EUROPIUM-BASED PROTEIN STAINS

(75) Inventors: Zhenjun Diwu; Wayne F. Patton, both of Eugene, OR (US)

(73) Assignee: Molecular Probes, Inc., Eugene, OR (US)

( * ) Notice: Subject to any disclaimer, the term of this patent is extended or adjusted under 35 U.S.C. 154(b) by 0 days.

(21) Appl. No.: 09/652,905

(22) Filed: Aug. 30, 2000

Related U.S. Application Data

(60) Provisional application No. 60/151,684, filed on Aug. 31, 1999.

(51) Int. Cl.$^7$ .................................................. G01N 21/64
(52) U.S. Cl. ............................. 436/86; 436/89; 436/172
(58) Field of Search ................................ 436/86, 87, 88, 436/89, 90, 172, 111, 112

(56) References Cited

U.S. PATENT DOCUMENTS

| | | |
|---|---|---|
| 4,058,732 | 11/1977 | Wieder . |
| 4,374,120 | 2/1983 | Soini et al. . |
| 4,637,988 | 1/1987 | Hinshaw et al. . |
| 5,260,050 * | 11/1993 | Ranney ..................................... 424/9 |
| 5,262,299 | 11/1993 | Evangelista et al. . |
| 5,312,922 | 5/1994 | Diamandis . |
| 5,316,906 | 5/1994 | Haugland et al. . |
| 5,321,130 | 6/1994 | Yue et al. . |
| 5,410,030 | 4/1995 | Yue et al. . |
| 5,453,356 * | 9/1995 | Bard et al. ............................... 435/6 |
| 5,578,498 | 11/1996 | Singh et al. . |
| 5,616,502 | 4/1997 | Haugland et al. . |
| 5,696,240 * | 12/1997 | Vallarino et al. ....................... 534/15 |
| 5,714,327 | 2/1998 | Houthoff et al. . |

FOREIGN PATENT DOCUMENTS

| | | |
|---|---|---|
| WO 89/10975 | 11/1989 | (WO) . |
| WO 90/00623 | 1/1990 | (WO) . |
| WO 92/16839 | 10/1992 | (WO) . |
| WO 93/06482 | 4/1993 | (WO) . |
| WO 94/24213 | 10/1994 | (WO) . |
| WO 97/20213 | 6/1997 | (WO) . |
| WO 0025139 * | 5/2000 | (WO) . |

OTHER PUBLICATIONS

Daban et al., Anal. Biochem. 199, 169 (1991).
M.J. Lim, et al., Anal. Biochem. 245, 184–195 (1997).
McWhinnie et al., Adv. Inorg. Chem. Radiochem. 12, 135 (1969).
J. Chem. Soc. Dalton Trans. 2247 (1985).
"Advanced Organic Chemistry, Reactions, Mechanisms and Structures" 3$^{rd}$ Ed. pp. 435–441, New York, 1985, J. March, Ed. Wiley–Interscience.
Patton et al., Analytical Biochemistry 220, 324–335 (1994).
Hill et al. Analytical Biochemistry 216, 439–443 (1994).
Copeland, Analytical Biochemistry 220 218–219 (1994).
Siepak, Analytica Chimica Acta 218, 143–149 (1989).
Evangelista et al. Clinical Biochemistry 21, 173–178 (1988).
Siepak, Analyst 114, 529–531 (1989).
Patton et al. Methods in Molecular Biology vol. 112: 2–D Proteome Analysis Protocols, A. J. Link, Ed. Humana Press Inc., Totawa, NJ; 331–339 (1999).
Castellano et al. Photochemistry and Photobiology 67(2), 179–183 (1998).

* cited by examiner

*Primary Examiner*—Jeffrey Snay
(74) *Attorney, Agent, or Firm*—Anton Skaugset; Allegra Helfenstein

(57) ABSTRACT

The invention relates to the staining of amine-containing polymers, including including peptides, polypeptides, and proteins, in gels and on solid supports, using complexes of europium (3+).

25 Claims, 2 Drawing Sheets

DETECTION METHOD USING LUMINESCENT EUROPIUM-BASED PROTEIN STAINS

This application claims the benefit of provisional application Ser. No. 60/151,684, filed Aug. 31, 1999, which is hereby incorporated by reference.

FIELD OF THE INVENTION

The invention relates to the luminescent staining of poly(amino acids), in gels and on solid supports, using complexes of europium (III).

BACKGROUND

Detection and analysis of poly(amino acids) is important in a variety of commercial and research applications. As used herein, a poly(amino acid) is any homopolymer or heteropolymer of amino acids, including peptides and proteins. Typically, poly(amino acids) are detected and characterized using gel electrophoresis, by solution quantitation assays or by detection on solid supports, such as filter membranes. Small amounts of poly(amino acids) are generally not visible to the naked eye, and must be stained before they can be localized and identified.

Two of the most common methods of staining poly(amino acids) in gels are COOMASSIE Brilliant Blue staining (hereafter referred to as CBB staining) and silver staining. For particular poly(amino acids), silver staining is approximately 100- to 1000-fold more sensitive than CBB staining, but both share some disadvantages. CBB staining and silver staining are time-consuming and yield a narrow range of linear response for densitometric quantitation. Also, the stained gels cannot be blotted for further analysis.

Furthermore, both CBB staining and silver staining are colorimetric—proteins are detected by the presence of colored or opaque bands in the electrophoresis gel. The use of luminescent reagents to detect proteins offers the possibility of greatly enhanced sensitivity and increased linear quantitation range, while simultaneously increasing the ease of use of the staining reagent. By "luminescent" is meant any reagent that is fluorescent, phosphorescent, chemiluminescent, or electroluminescent.

Fluorescent reagents have previously been used for staining poly(amino acids), such as the dye Nile red (9-diethylamino-5H-benzo(α)phenoxazine-5-one) (see for example Daban et al., ANAL. BIOCHEM. 199, 169 (1991)). Selected styryl and merocyanine dyes have also been utilized as fluorescent stains for poly(amino acids) in gels, on membranes or other supports (U.S. Pat. No. 5,616,502 to Haugland et al., hereby incorporated by reference). While staining with small organic dyes is very rapid, relatively insensitive to poly(amino acid) composition, does not require destaining, and is typically very sensitive, organic fluorescent dyes typically suffer from the drawback of high background noise.

Selected metal complexes exhibit long-lived luminescent emission, and permit "time-resolved" detection at a point after illumination, reducing the interference from short-lifetime fluorescence in the sample to essentially zero.

Luminescent metal chelate stains including europium complexed to bathophenanthroline disulfonate have been described (see M. J. Lim, et al., ANAL. BIOCHEM. 245, 184–195 (1997), and International Publication No. WO 97/20213). The europium-based stain has been shown to be useful for detection of low-nanogram quantities of proteins immobilized on nitrocellulose or polyvinylidene difluoride (PVDF) membranes (patent application Ser. No. 09/080,626, LUMINESCENT PROBES FOR PROTEIN DETECTION, filed May 18, 1998 by Patton et al., now abandoned, incorporated by reference). This method of staining proteins is highly resistant to photobleaching and compatible with popular downstream biochemical characterization procedures including immunoblotting, lectin blotting and mass spectrometry. Disadvantages of the bathophenanthroline disulfonate/europium stain are that the dye can only be visualized using 302 nm UV-B illumination, and exhibits intense blue fluorescence as well as the desired emission maxima of 595 and 615 nm. In addition, the bathophenanthroline disulfonate/europium stain exhibits two emission peaks of roughly the same intensity at 595 and 615 nm, requiring detection across a 24 nm emission window to collect all of the luminescent signal.

Another recently developed luminescent metal chelate stain utilizes ruthenium instead of europium complexes to detect proteins (as described in copending patent application Ser. No. 09/429,739, filed Oct. 27, 1999 by Bhalgat et al., incorporated by reference). The stain offers many of the same advantages as the bathophenanthroline disulfonate/europium stain, but with the additional benefits of higher detection sensitivity, compatibility with most laser-based gel scanners, compatibility with UV epi- and trans-illuminators and minimal cross-reactivity with nucleic acids. However, the ruthenium-based complex exhibits a fairly broad emission peak (100 nm) that may complicate multicolor visualization procedures, and is difficult to remove from bound protein—a significant drawback in some applications.

The europium complexes of the instant invention are roughly 10 times brighter than the bathophenanthroline disulfonate/europium stain described above. Furthermore, the intense blue fluorescence that resulted from the presence of uncomplexed ligand has been eliminated because the compounds of the instant invention are substantially more thermodynamically stable. Proteins stained with the europium complexes of the invention are readily visualized with either UV-A, UV-B, or UV-C illumination, and display a single narrow emission peak. The instant complexes are also easily removed from proteins by increasing the solution pH of the stained sample, making them fully compatible with matrix-assisted laser desorption mass spectrometry, biotin/streptavidin detection systems and immunoblotting.

The europium complexes used to practice the method of the instant invention are highly stable, even in relatively dilute solution, and bind strongly to proteins in solution, on membranes, in biological cells, in moderately acidic solutions, and in electrophoretic gels, yielding bright, long-lifetime, visible luminescence. The complexes exhibit exceptional photostability, allowing long exposure times for maximum sensitivity. The complexes are readily removed from proteins by incubating membranes at mildly alkaline pH. The reversibility of the protein staining procedure allows for subsequent biochemical analyses, such as immunoblotting, biotin-streptavidin detection and mass spectrometry.

TABLE 1

Comparison of Luminescent Protein Stains:

| Characteristic: | Compound 1 | Eu(BPDS)$_3^{3-}$† | Ru(BP)$_2$(BPDS)‡ |
|---|---|---|---|
| Excitation source compatibility | UV-A (360 nm), UV-B (302 nm) UV-C (254 nm) Epi-illumination[1] | UV-B (302 nm) Epi-illumination[2] | UV-B (302 nm), 450–532 nm Epi- or trans-illumination |
| Emission source compatibility | Em$_{max}$ = 615 nm | Em$_{max}$ = 615 nm | Em$_{max}$ = 610 nm |

TABLE 1-continued

Comparison of Luminescent Protein Stains:

| Characteristic: | Compound 1 | Eu(BPDS)$_3^{3-}$† | Ru(BP)$_2$(BPDS)‡ |
|---|---|---|---|
| Reversibility of staining | Readily reversible | Readily reversible | Fairly permanent |
| Emission bandwidth at half height | 8 nm | 28 nm (both peaks) | 100 nm |
| Stability | Stable to dilution | Very unstable | Stable to dilution |
| Time-resolved fluorescence | T½ = 25–50 μsec (theoretical) | T½ = 25–50 μsec (theoretical) | T½ = 1–2 μsec (theoretical) |
| Interaction with protein | Binds protein | Binds protein | Binds protein |
| Sensitivity for membrane-bound proteins | 6 ng/mm$^2$ | 47 ng/mm$^2$ | 12 ng/mm$^2$ |

†BPDS = bathophenanthroline disulfonic acid
‡BP = bathophenanthroline
[1]Excitation maximum is about 355 nm
[2]Excitation maximum is about 290 nm

SUMMARY OF THE INVENTION AND DESCRIPTION OF THE PREFERRED EMBODIMENTS

Figure 1:
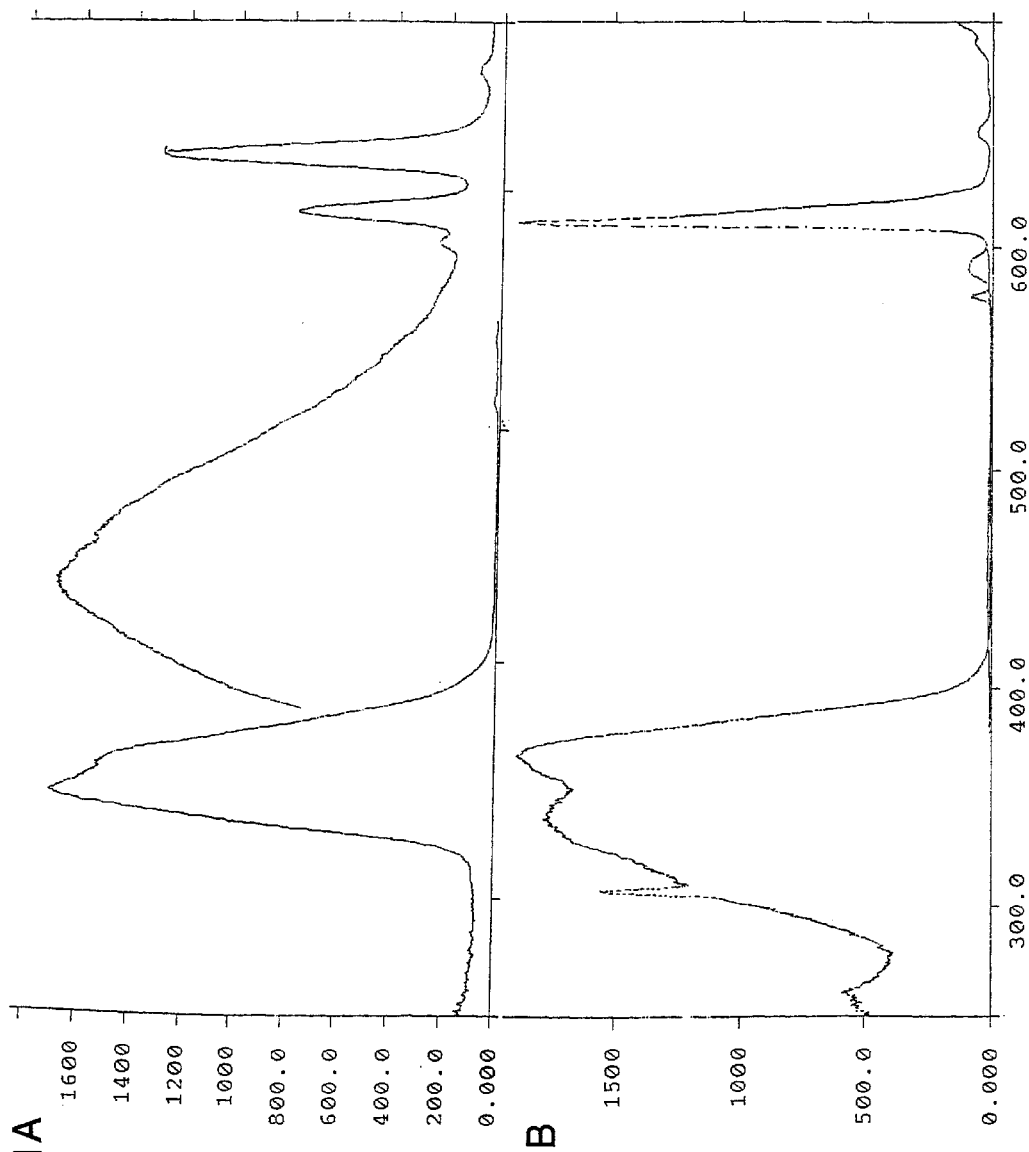
FIG. 1: Comparison of the fluorescence excitation/emission spectra of bathophenanthroline disulfonate/europium complex with Compound 1. (A.) Excitation/emission profile of bathophenanthroline disulfonate/europium (III). (B.) Excitation/emission spectra of Compound 1. The thermodynamic instability of the bathophenanthroline disulfonate/europium complex leads to an equilibrium between uncomplexed and complexed bathophenanthroline disulfonate. This results in a strong emission peak at 446 nm due to the presence of uncomplexed chelate. Compound 1 is a more stable complex and has no spurious blue emission peak.

The invention relates to the staining of poly(amino acids) by europium complexes. One aspect of the invention is novel staining mixtures comprising a europium ion coordinated with a plurality of ligands. Another aspect of the invention is the use of the selected europium complexes for staining poly(amino acids).

The Europium Complex

To practice the invention, a composition comprising selected europium ligand complexes is used. The complexes of the invention comprise a europium (III) ion, at least one polydentate nitrogen donor ligand, and at least one acetylacetonate-derived ligand (referred to as acac ligands). Any ligand of the complex is optionally substituted by an anionic or cationic moiety.

As is well known for transition metal complexes, a given complex may exist as a mixture of stereoisomers. The absolute configuration of ligands around the europium ion does not appear to influence the ability of the complex to stain poly(amino acids).

Covalent Linkage

As used herein, a covalent linkage is optionally a single covalent bond, or is a combination of stable chemical bonds, optionally including single, double, triple or aromatic carbon-carbon bonds, as well as carbon-nitrogen bonds, nitrogen-nitrogen bonds, carbon-oxygen bonds, carbon-sulfur bonds, phosphorus-oxygen bonds, and phosphorus-nitrogen bonds. The covalent linkage typically includes ether, thioether, carboxamide, sulfonamide, urea, urethane or hydrazine moieties. In one embodiment, the covalent linkage incorporates a platinum atom, such as described in U.S. Pat. No. 5,714,327 (incorporated by reference). Preferred covalent linkages have 1–20 nonhydrogen atoms selected from the group consisting of C, N, O, P, and S; and are composed of any combination of ether, thioether, amine, ester, carboxamide, sulfonamide, hydrazide bonds and aromatic or heteroaromatic bonds. Preferably the covalent linkage is a combination of single carbon-carbon bonds and carboxamide or thioether bonds. The longest linear segment of the covalent linkage preferably contains 4–10 nonhydrogen atoms, including one or two heteroatoms. Examples of the covalent linkage include substituted or unsubstituted polymethylene, arylene, alkylarylene, arylenealkyl, or arylthio. In one embodiment, the covalent linkage contains 1–6 carbon atoms; in another, it is a thioether linkage. In yet another embodiment, it is or incorporates the formula —(CH$_2$)$_a$(CONH(CH$_2$)$_b$)$_z$—, where a has any value from 0–5, b has any value from 1–5 and z is 0 or 1.

The Polydentate Nitrogen Donor Ligand

Aromatic nitrogen heterocycles, and other derivatives of ammonia are classical ligands in coordination chemistry, and typically bind to transition metals via electron pair donation from the nitrogen atom. Ligands that possess more than one nitrogen atom that can bind to a metal atom are known as polydentate ligands. Classical examples of polydentate nitrogen-based ligands include, among others, ethylenediamines, tetramethylethylenediamines, pyridines, polypyridyls (including bipyridyls, terpyridyls and others), quinolines, and phenanthrolines. These nitrogen donor ligands are good ligands for transition metals over a range of oxidation states (see for example McWhinnie et al., ADV. INORG. CHEM. RADIOCHEM. 12, 135 (1969)).

In the instant invention, the nitrogen donor ligand comprises two heteroaromatic rings that are linked by a single covalent bond, or by an appropriate covalent linkage. In another embodiment, the nitrogen donor ligand comprises two heteroaromatic rings that are linked by an additional fused aromatic ring. In yet another embodiment, the nitrogen donor ligand comprises three heteroaromatic rings that are attached in series by single covalent bonds, or by appropriate covalent linkages. In any embodiment, the heteroaromatic rings of the ligand are optionally substituted as described below, and optionally incorporate one or more additional heteroatoms that are N, O, or S. Where the ligands of the invention incorporate multiple heteroaromatic rings, they are typically polydentate, and bind to the europium ion via the heteroaromatic ring nitrogen atoms.

The nitrogen donor ligand of the invention is optionally substituted by a wide variety of substituents, including alkyl, aryl, and heteroaryl substituents, alkenes, alkynes, heteroaryl, halogens, ethers, thioethers, amides, esters, acids, and nitrogen containing groups. In one embodiment, the ligand substituents are simple substituents such as H, halogen, or CN. In another embodiment, allowed substituents include alkyl, perfluoroalkyl, or alkoxy having 1–6 carbon atoms; carboxy (—COOH), carboxyalkyl, carboxyalkoxy, carboxyalkylamino, or carboxylalkylthio, each having 2–7 carbons; sulfonate (a sulfonic acid, SO$_3$H, or salt of sulfonic acid where the salt is typically an alkali metal cation or an ammonium cation), or sulfoalkyl having 1–6 carbons. Other ligand substituents are optionally amino, salt of amino (where the counterion is a halide, sulfate, sulfonate, substituted sulfonate, phosphate, perchlorate, tetrafluoroborate, tetraphenylboride, or an anion of an aromatic or aliphatic carboxylic acid), alkylamino or dialkylamino, where each alkyl group has 1–6 carbons. Still other ligand substituents are optionally aryl or heteroaryl. Alternatively, two or more ligand substituents optionally form additional fused rings that are themselves optionally substituted by the ligands described above.

An aryl substituent, as used herein, is a six-membered aromatic ring, attached by a single covalent bond, which is typically phenyl or substituted phenyl, but also encompasses simple aromatic substituents such as naphthyls and substituted naphthyls. Heteroaryl, as used herein, is an aromatic group that contains at least one heteroatom (a non-carbon atom forming part of the ring structure). A heteroaryl substituent is optionally a 5- or 6-membered ring, and is a single ring structure or a fused 2- or 3-ring structure. A heteroaryl substituent optionally contains one or more heteroatoms, e.g. pyrrolyl, pyridyl, thienyl, or furanyl (single ring, single heteroatom), or oxazolyl, isoxazolyl, oxadiazolyl, or imidazolyl (single ring, multiple heteroatoms), or benzoxazolyl, benzothiazolyl, or benzimidazolyl, (multi-ring, multiple heteroatoms), or quinolyl, benzofuranyl or indolyl (multi-ring, single heteroatom). Preferred heteroaryl substituents are thienyl, pyridyl and quinolyl. Aryl and heteroaryl substituents are typically used to modify the spectral properties, affinity, selectivity, solubility or reactivity of the resulting metal complex, or any combination of these factors. Both aryl and heteroaryl substituents of the instant ligand are independently and optionally substituted one or more times as described for the heteraromatic rings of the ligands of the invention, including halogen; sulfonate; phosphonate; phosphate; boronate; alkyl, perfluoroaLkyl or alkoxy (each having 1–6 carbons); or carboxy, carboxyalkyl, carboxyalkoxy, carboxyalkylamino, or carboxyalkylthio (having 2–7 carbons).

Additional selected ring substituents are typically utilized to alter the solubility of the resulting metal complex in either aqueous or organic solvents, to modify the spectral or binding properties of the metal complex with either poly (amino acids), or to modify the electronic environment of the metal center. For instance, the greater the degree of sulfonation on the ligand, the greater the degree of aqueous solubility the resulting metal complex typically possesses. The additional substitution of ammonium salts, carboxy, carboxyalkyl, carboxyalkoxy, carboxyalkylamino, or carboxyalkylthio or other highly polar substituents also results in enhanced aqueous solubility, improved protein binding or other desirable features.

In one embodiment, the polydentate nitrogen donor ligand present in the complexes of the invention is substituted by one or more anionic moieties. Anionic moieties are functional groups that possess a negative ionic charge at the pH ranges used for the instant method. Anionic moieties include, without limitation, phosphate, phosphonate, carboxylate, boronate, sulfate and sulfonate. Typically, the ligand is substituted by at least one sulfonate moiety. The presence of the acac ligands in the complex (formally negatively charged) typically balances the positive charge of the europium ion, and so the charge of the sulfonate groups results in an overall negatively charged complex. The charge of the complex is therefore balanced by the charge of a cationic counterion or counterions. At physiological or lower pH, sulfonate moieties are typically present as the sulfonate ion. The sulfonate groups present on the ligands of the invention may be bound directly to an aromatic nitrogen heterocycle, or be bound via a ring substituent, such as a sulfophenyl or polysulfophenyl substituent. The location of sulfonic acid substitution on the ligand is apparently not critical to the staining efficacy of the resulting metal complex, and complexes that incorporate mixtures of ligand isomers typically function as well as isomer-free complexes.

In another embodiment, the polydentate nitrogen donor ligands present in the complexes of the invention are substituted by one or more cationic moieties. Cationic moieties are functional groups that possess a positive ionic charge at the pH ranges used for the instant method. Cationic moieties typically include quaternized ammonium groups, such as trialkylammonium, pyridinium, or quinolinium substituents. Typically, the charge of the ammonium groups is partially or fully balanced by the charge present on one or more anionic counterions. The ammonium groups present on the ligands of the invention may be bound directly to an aromatic nitrogen heterocycle, or be bound via a ring substituent, such as a phenyl substituent. More typically, the ammonium group is bound via an appropriate covalent linkage.

Preferred nitrogen donor ligands of the invention include, without limitation pyridines, bipyridines, ter-pyridines, phenanthrolines, bathophenanthrolines, imidazoles, pyrroles, pyrazoles, indazoles, triazoles, pyrazines, pyrinidines, pyridazines, purines, porphyrins, and phthalocyanines. Particularly preferred are bipyridines, ter-pyridines, phenanthrolines, and bathophenanthrolines. Most preferred are phenanthrolines and bathophenanthrolines. Nitrogen containing rings may also be further modified, such as by fusion to aromatic rings, for example to yield a benzotriazole or a biquinoline.

Preferably, the nitrogen donor ligands of the invention possess at least two pyridyl rings, according to the general formula

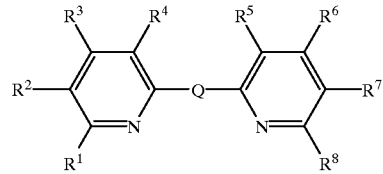

where the pyridyl rings have the primary ring substituents $R^1$, $R^2$, $R^3$, $R^4$, $R^5$, $R^6$, $R^7$, and $R^8$ that are independently selected from H, halogen, CN, alkyl, perfluoroalkyl, or alkoxy having 1–6 carbon atoms; carboxy (—COOH), carboxyalkyl, carboxyalkoxy, carboxyalkylamino, carboxylalkylthio, each having 2–7 carbons, amino, salt of amino (where the counterion is a halide, sulfate, sulfonate, phosphate, perchlorate, tetrafluoroborate, tetraphenylboride, or an anion of an aromatic or aliphatic carboxylic acid), alkylamino or dialkylamino, where each alkyl group has 1–6 carbons. Where the ligand is sulfonated, at least one substituent is sulfonic acid, or salt of sulfonic acid. Still other ring substituents are optionally aryl or heteroaryl. Typically, the ligand has no more than two aryl or heteroaryl substituents, which are usually attached at $R^1$, $R^3$, $R^6$, and/or $R^8$, preferably at $R^3$ and $R^6$.

Each heteroaromatic ring of the ligand is optionally substituted by an additional fused aromatic ring. Any two adjacent heteroaromatic ring substituents taken in combination are optionally an additional fused aromatic ring; for example, $R^1$ and $R^2$ taken in combination, or $R^5$ and $R^6$ taken in combination. There are no more than two additional fused aromatic rings on the ligand, one on each heteroaromatic ring. Ligands that possess two additional fused aromatic rings may be symmetrically or unsymmetrically substituted. The fused aromatic ring substituents are independently and optionally substituted by halogen; sulfonic acid or salt of sulfonic acid; cyano; alkyl, perfluoroalkyl or alkoxy (each having 1–6 carbons); amino; alkylamino (having 1–6 carbons); dialkylamino (having 2–12 carbons); carboxy; or carboxyalkyl, carboxyalkoxy, carboxyalkylamino, or carboxyalkylthio (each having 2–7 carbons). Selected (but not exclusive) examples of some metal ion-binding moieties having additional fused rings are shown below.

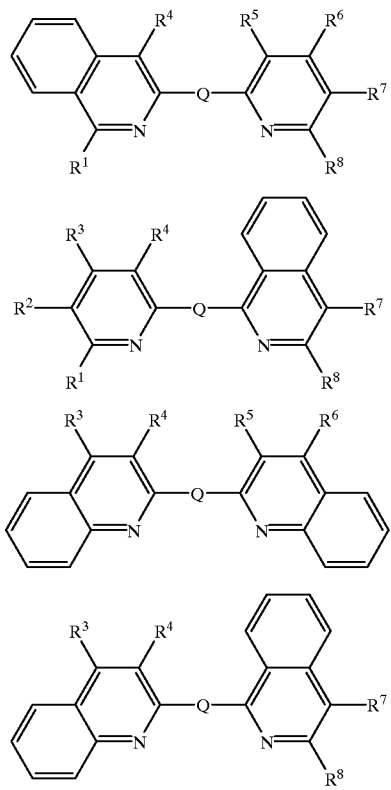

The aryl, heteroaryl, and additional fused ring substituents on the ligand optionally serve as attachment points for sulfonic acids or salts of sulfonic acids.

In one embodiment of the invention, Q is a single covalent bond, such that the resulting ligand is a bipyridyl-based chelator. Ligands that are bipyridyls have the general structure:

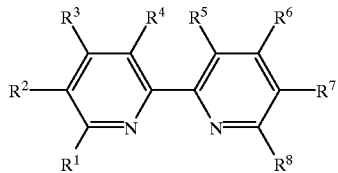

where $R^1$–$R^8$ are as defined previously.

In another embodiment of the invention, Q is a formal single bond, and $R^4$ and $R^5$ when taken in combination are —$CR^9$=$CR^{10}$—, such that the ligand is an aromatic phenanthroline-based chelator having the general formula:

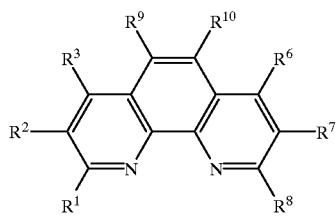

where $R^1$–$R^3$ and $R^6$–$R^8$ are as defined previously, and phenanthroline substituents $R^9$ and $R^{10}$ are independently H; alkyl, perfluoroalkyl, or alkoxy having 1–6 carbon atoms; a sulfonic acid, a salt of sulfonic acid; an amino, alkylamino or dialkylamino, where each alkyl group has 1–6 carbons; a carboxy; or carboxyalkyl, carboxyalkoxy, carboxyalkylamino or carboxyalkylthio having 2–7 carbons; an aryl or heteroaryl; halogen; or CN. Typically, one of $R^9$ and $R^{10}$ serves as the attachment point for a sulfonic acid or salt of sulfonic acid, and all other ring substituents are hydrogen, phenyl or phenyl substituted one or more times by a sulfonic acid or salt of sulfonic acid. Preferably, $R^3$ or $R^6$ or both are substituted by phenyl that is itself optionally substituted by a single sulfonic acid or salt of sulfonic acid. In a preferred embodiment, each of $R^1$ and $R^8$ are independently carboxy or phosphate, more preferably, each of $R^1$ and $R^8$ are carboxy.

When the ligand is a phenanthroline-based chelator, adjacent heteroaromatic ring substituents are optionally combined to form additional fused aromatic rings, excepting that $R^4$ and $R^5$ are no longer available to form additional fused rings with $R^3$ and $R^6$, respectively. Additional fused aromatic rings are therefore only available using combinations of $R^1$, $R^2$, $R^3$, $R^6$, $R^7$ and $R^8$. Typically the phenanthroline-based ligand does not contain additional fused rings.

In another embodiment of the invention, Q is —$(CR^{11}_2)_a$—$X_b$—$(CR^{12}_2)_c$—, such that the ligand is a bis-pyridyl-based chelator. In this embodiment, a, b and c are each 0 or 1, excepting that when b=1, a+c must equal 0 or 2. Selected examples of bis-pyridyl-based ligands are shown below.

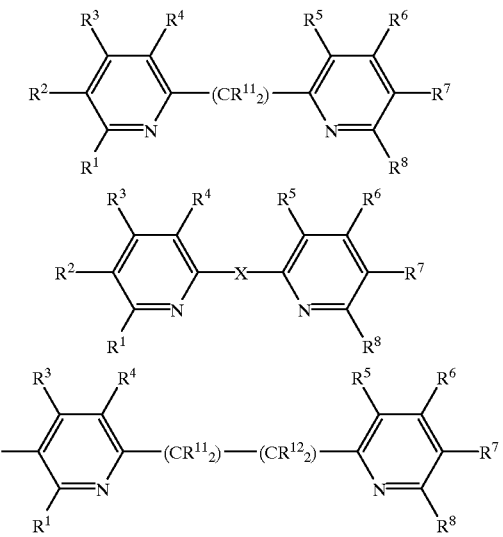

-continued

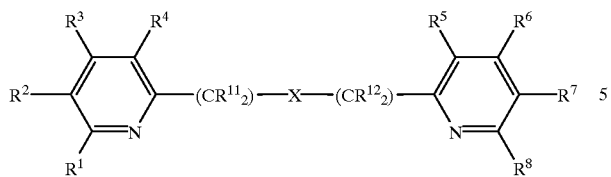

Each $R^{11}$ and $R^{12}$ is optionally and independently H or alkyl having 1–6 carbon atoms. Typically, each $R^{11}$ and $R^{12}$ is hydrogen.

The element X is optionally O or S, yielding an ether or thioether bridge, respectively. Alternatively, X is $NR^{13}$, where $R^{13}$ is H, $C_1$–$C_6$ alkyl. Alternatively, $R^{13}$ is phenyl that is optionally further substituted one or more times in any combination by alkyl, perfluoroalkyl, or alkoxy having 1–6 carbon atoms; sulfonic acid, salt of sulfonic acid; $NO_2$; amino, alkylamino or dialkylamino, where each alkyl group has 1–6 carbons; carboxy; carboxyalkyl, carboxyalkoxy, carboxyalkylamino or carboxyalkylthio having 2–7 carbons; halogen, or CN. In yet another embodiment, X is —$CR^{14}R^{15}$—, yielding a trimethylene bridge, where $R^{14}$ and $R^{15}$ are independently H or alkyl having 1–6 carbons. Additionally, either of $R^{14}$ and $R^{15}$ optionally serves as an attachment point for a sulfonic acid or salt of sulfonic acid. Typically, Q is —$CR^{11}_2$—$NR^{13}$—$CR^{12}_2$—, and $R^{13}$ is phenyl or substituted phenyl. Where $R^{13}$ is phenyl or substituted phenyl, it is optionally substituted by sulfonic acid or salt of sulfonic acid, as shown below:

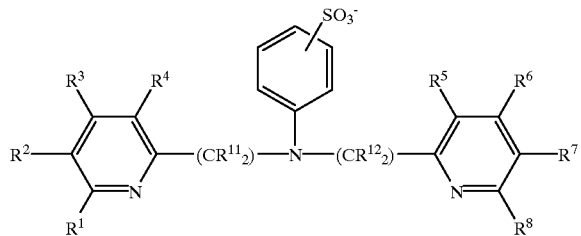

In an alternate embodiment of the invention, Q is a 2,6-disubstituted pyridyl, to yield a ligand having a terpyridyl-based complexing group, according to the following structure:

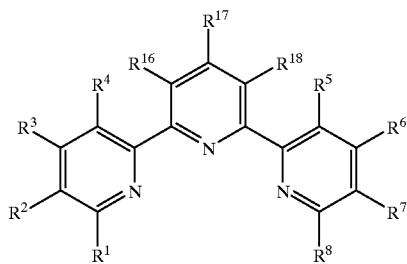

where $R^1$–$R^4$ and $R^5$–$R^8$ are as defined previously. In this embodiment, the substituents $R^{16}$, $R^{17}$, and $R^{18}$ are independently H; alkyl, perfluoroalkyl, or alkoxy having 1–6 carbon atoms; sulfonic acid, salt of sulfonic acid; amino, alkylamino or dialkylamino, where each alkyl group has 1–6 carbons; carboxy; or carboxyalkyl, carboxyalkoxy, carboxyalkylamino, or carboxyalkylthio having 2–7 carbons; halogen, or CN. Alternatively, one or more of $R^{16}$, $R^{17}$, and $R^{18}$ serves as the attachment point for sulfonic acid or salt of sulfonic acid. Typically $R^{16}$, $R^{17}$, and $R^{18}$ are hydrogen or sulfonic acid. Preferably $R^{16}$ and $R^{18}$ are hydrogen and $R^{17}$ is sulfonic acid.

Preferably, the nitrogen donor ligand is a phenanthroline, preferably a bathophenanthroline, most preferably a disulfonated bathophenanthroline.

Acetylacetonate Ligands

In addition to the polydentate nitrogen donor ligand, the complexes of the invention are associated with at least one bidentate ligand formally derived from the acetylacetonate anion (acac). These acetylacetonate ligands, which may be the same or different, have the formula

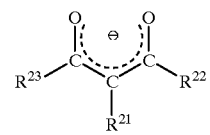

The negative charge on the acac ligand is delocalized, resulting in a conjugated system that is a resonance hybrid of the following formal structures:

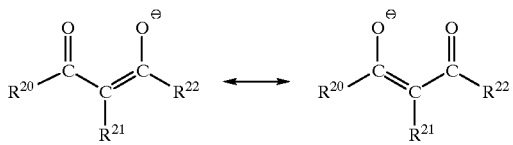

Although a particular acac ligand may be drawn herein as the resonance structure or one or the other formal structures, it is recognized that each representation is an equivalent representation of the actual conjugated resonance structure.

The $R^{20}$ substituent is an alkyl having 1–6 carbons that is optionally and independently substituted one or more times by halogen, cyano, nitro, sulfonate, amino, salt of amino, substituted or unsubstituted aryl or heteroaryl (as defined above); alkene, alkyne, alkoxide, ether, thioether, carboxy (—COOH), carboxyalkyl, carboxyalkoxy, carboxyalkylamino, or carboxylalkylthio, each having 2–7 carbons; amino, or salt of amino. Alternatively, $R^{20}$ is an alkyl having 1 carbon that is substituted by an electron withdrawing group (EWG). In a preferred embodiment, $R^{20}$ is a perfluorinated alkyl having 1–6 carbons. More preferably, $R^{20}$ is a trifluoromethyl.

The $R^{21}$ substituent is H, halogen, cyano, nitro, sulfonate, amino, salt of amino, substituted or unsubstituted aryl or heteroaryl (as defined above); alkene, alkyne, alkoxide, ether, thioether, carboxy (—COOH), carboxyalkyl, carboxyalkoxy, carboxyalkylamino, or carboxylalkylthio, each having 2–7 carbons; amino, or salt of amino. Alternatively, $R^{21}$ is an electron withdrawing group (EWG). Typically, $R^{21}$ is H.

The $R^{22}$ substituent is a substituted or unsubstituted aryl or heteroaryl, as defined above. Preferably, $R^{22}$ is a substituted or unsubstituted phenyl, naphthyl, or thienyl. In one aspect of the invention, $R^{22}$ is optionally substituted by one or more anionic moieties or cationic moieties (as defined above). In one embodiment, $R^{22}$ is a naphthyl that is substituted by one or more sulfonate moieties. Most preferably, $R^{22}$ is a naphthyl. Where $R^{22}$ is a naphthyl, it is preferably a 2-naphthyl.

To insure that the resulting europium complex is thermodynamically robust, it is e preferred that either $R^{21}$ is an EWG, or $R^{20}$ is a $C_1$-alkyl that is substituted by an EWG. As used herein, an EWG is a substituent that is more strongly electron-withdrawing than a phenyl substituent at the same position. Examples of typical EWG substituents include iodo, bromo, chloro, fluoro, trifluoromethyl, cyano, acetyl, nitro, alkoxy, carboxy, hydroxy, and perfluorophenyl. Preferred EWG substituents include fluoro, trifluoromethyl, and cyano.

In a preferred embodiment, the acac ligand has the formula

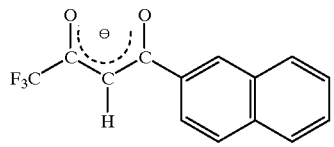

The complexes of the invention comprise a europium (III) ion complexes with at least one polydentate nitrogen donor ligand and at least one acac ligand. Preferably, the complexes of the invention comprise a single polydentate nitrogen donor ligand, and the remaining ligands associated with the europium ion are acac ligands, which may be the same or different. In one aspect of the invention, the polydentate nitrogen donor ligand is a bidentate nitrogen donor ligand, and the europium ion is additionally associated with four acac ligands, which may be the same or different. Most preferably, the bidentate nitrogen donor ligand is a phenanthroline or bathophenanthroline.

In one embodiment of the invention, the polydentate nitrogen donor ligand or one or more acac ligands, or both, is substituted by one or more cationic moieties. In another preferred embodiment of the invention, either the polydentate nitrogen donor ligand or one or more acac ligands, or both, is substituted by one or more anionic moieties, preferably carboxy or sulfonate, most preferably sulfonate.

Selected embodiments of the europium complexes of the invention are provided in Table 2. Each of the selected embodiments have the general formula

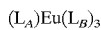

where $L_A$ is a polydentate nitrogen donor ligand, and $L_B$ is an acac ligand. Each compound is optionally associated with one or more counterions that balance the overall charge of the europium complex.

TABLE 2

Selected embodiments of europium complexes having the formula $(L_A)Eu(L_B)_3$

TABLE 2-continued

Selected embodiments of europium complexes having the formula $(L_A)Eu(L_B)_3$

| $L_A$ (Ligand A) | $L_B$ (Ligand B) | Compound No. |
|---|---|---|
| 4,7-diphenyl-1,10-phenanthroline | 1-(3,5-disulfonaphth-7-yl)-4,4,4-trifluoro-1,3-butanedionate | 3 |
| bis(trimethylammoniumacetylhydrazido)-4,4'-bipyridine derivative | 1-(naphth-2-yl)-4,4,4-trifluoro-1,3-butanedionate | 4 |
| 4,7-diphenyl-1,10-phenanthroline | 1-(thien-2-yl)-4,4,4-trifluoro-1,3-butanedionate | 5 |
| 4,7-bis(4-sulfonatophenyl)-1,10-phenanthroline-2,9-dicarboxylate | 1-(naphth-2-yl)-4,4,4-trifluoro-1,3-butanedionate | 6 |

TABLE 2-continued

Selected embodiments of europium complexes having the formula (L$_A$)Eu(L$_B$)$_3$

| L$_A$ (Ligand A) | L$_B$ (Ligand B) | Compound No. |
|---|---|---|
| [structure: 4,7-diphenyl-2,9-dicarboxylate-1,10-phenanthroline] | [structure: trifluoromethyl-naphthoyl acac enolate] | 7 |

Synthesis of the Europium Complex

The preparation of transition metal complexes incorporating nitrogen donor ligands and acac ligands is generally well known in the art. The synthesis of the complexes of the invention follows well-known procedures for preparation of similar complexes.

The typical synthesis consists of mixing, and if necessary, heating a solution of the appropriate metal chloride in the presence of the desired nitrogen donor ligand and acac ligand. Ligands derived from acetylacetonate are generally deprotonated by strong base prior to complexation with the europium ion (see Example 1). Mixed ligand complexes are typically prepared by heating the metal chloride in the presence of a mixture of the desired ligands in the desired ratios. The resulting products typically occur in a statistical distribution, and can be isolated by methods known in the art. Alternatively, the chloride ions are displaced in a stepwise fashion by the selected ligands, resulting in the controlled synthesis of the desired isomer.

Many nitrogen donor ligands and acac ligands suitable for use in the instant invention are commercially available. Where a desired ligand is not readily available, it is often readily synthesized from commercially available starting materials, or the ligand is synthetically modified prior to complexation with the metal.

Sulfonation of heteroaromatic ligands occurs by methods well known in the art, typically using sulfuric acid, filming sulfuric acid, or chlorosulfonic acid. In the case of bipyridyl ligands, direct sulfonation is typically not effective. For example, sulfonated bipyridyls are typically prepared by thiolation of bipyridyl followed by oxidation to the sulfonic acid (for example, J. CHEM. SOC. DALTON TRANS. 2247 (1985)).

The desired acac ligand precursor is generally prepared by the Claizen condensation method. The reaction of a fluorinated alkyl methyl ketone with a selected ester in the presence of base such as sodium methoxide readily give the desired beta-diketone (for a general review, see Advanced Organic Chemistry, Reactions, Mechnisms and Structures, pages 435–441, ed. by J. March, Wiley-Interscience, 3 rd. Ed., New York, 1985).

Method of Use

The present invention utilizes the metal complexes described above to stain an analyte, followed by detection of the stained analyte and optionally its quantification or other analysis. Typically the analyte is a polymer or macromolecule that incorporates primary, secondary, or tertiary amines, preferably primary or secondary amines. In a preferred aspect of the invention, the analyte is a polymer that is a poly(amino acid).

The analyte is stained by combining a sample mixture that is thought to contain the analyte, with a staining mixture that comprises one or more of the europium complexes described above that give a detectable luminescent optical response upon illumination.

In one aspect of the invention, the instant method of detecting an analyte comprising the steps of:

a) combining a sample mixture that is thought to contain the analyte with a staining mixture that contains one or more europium complexes to form a combined mixture;

wherein each europium complex independently comprises:
  i) a europium (III) ion;
  ii) at least one polydentate nitrogen donor ligand; and
  iii) at least one acetylacetonate ligand;

b) incubating the combined mixture for a time sufficient for the europium complexes in the staining mixture to associate with the analyte in the sample mixture to form a stained analyte complex that gives a detectable luminescence response upon illumination;

c) illuminating said stained analyte complex; and d) observing said luminescence response.

Additional steps are optionally and independently used in any combination, before, after or concurrently with staining, to provide for separation or purification of the analyte, for enhancing the detection of the analyte, for quantification of the analyte, for identification of a specific analyte or group of analytes for example by use of an immunological reagent such as an antibody or lectin.

In one embodiment, the analyte is a polymer that incorporates one or more amines, such as aminodextran, polyvinylpyrrolidone, or a starburst dendrimer. Preferably, the analyte is a polymer that is a poly(amino acid). Without wishing to be bound by theory, where the complex of the invention is substituted by one or more anionic moieties it is presumed that the anionic moieties of the metal complexes of the invention associate electrostatically with aliphatic amines present on poly(amino acids), which are typically protonated and positively charged at or below physiological pH. Therefore the complexes of the invention that are substituted on either the polydentate nitrogen donor ligand or on one or more acac ligands by at least one anionic moiety are useful for the detection and quantification of poly(amino acids) and other substances that incorporate amines, such as selected lipopolysaccharides.

Typically, the present invention is utilized to detect the desired analyte by combining a sample mixture that is thought to contain the analyte with a staining mixture that contains one or more of the metal complexes of the invention to form a combined mixture. The combined mixture is then incubated for a time sufficient for the metal complex in the staining mixture to associate with any analyte present in the sample mixture. The resulting stained analyte complex is then illuminated at a wavelength where the selected metal complex is excited, and the resulting optical response is detected.

Sample Mixture

The sample mixture contains or is suspected to contain an analyte of interest. Typically the sample mixture comprises a solid or semi-solid matrix, where the analyte is present on or within the matrix. In one embodiment, the sample mixture comprises a membrane, such as a filter membrane. In another embodiment, the sample mixture comprises an electrophoretic gel. The sample mixture optionally further comprises an aqueous solution, typically prepared with water (e.g. for pure proteins) or aqueous buffer, or is combined with an aqueous solution in the course of labeling. By aqueous solution is meant a solution that is predominantly water and retains the solution characteristics of water. Where the aqueous solution contains solvents in addition to water, water is typically the predominant solvent.

In one embodiment of the invention, the sample mixture comprises a membrane, such as a nitrocellulose or poly (vinylidene difluoride) membrane, wherein the analyte is applied to the membrane by blotting, spotting, or other methods.

The poly(amino acids) that are suitable for staining using this method include both synthetic and naturally occurring poly(amino acids), comprising both natural and unnatural amino acids. The poly(amino acids) of the invention include peptides, polypeptides and proteins. Poly(amino acids) that are labeled and analyzed according to the present method optionally incorporate non-peptide regions (covalently or non-covalently) including lipid (lipopeptides and lipoproteins), phosphate (phosphopeptides and phosphoproteins), and/or carbohydrate (glycopeptides and glycoproteins) regions; or incorporate metal chelates or other prosthetic groups or non-standard side chains; or are multi-subunit complexes, or incorporate other organic or biological substances, such as nucleic acids. The poly(amino acids) are optionally relatively homogeneous or heterogeneous mixtures of poly(amino acids). Preferably, the poly (amino acids) contain at least one basic amino acid such as lysine, arginine or histidine. In one aspect of the invention the poly(amino acids) are enzymes, antibodies, transcription factors, secreted proteins, structural proteins, nuclear proteins, fuision proteins, or binding factors, or combinations thereof. In another aspect of the invention, the poly (amino acids) comprise the proteome of a cell. In one embodiment, the method of the instant invention is both generally and specifically useful in performing many aspects of proteomics, that is, the determination of an accurate profile of protein abundance, structure and activity in a given cell or tissue sample.

The analytes in the sample mixture are optionally covalently or non-covalently bound to a solid or semi-solid surface, such as a glass slide, multi-well plate (such as a 96-well plate), plastic pin, polymeric membrane or bead, or semiconductor material, or they are unbound. The staining of an analyte that is bound to a substrate on a solid surface indicates the presence of the substrate as well as that of the analyte.

The desired analyte may be obtained from a variety of sources. Poly(amino acids) may be obtained from sources including biological fermentation media and automated protein synthesizers, as well as prokaryotic cells, eukaryotic cells, virus particles, tissues, and biological fluids. Suitable biological fluids include, but are not limited to, urine, cerebrospinal fluid, blood, lymph fluids, interstitial fluid, cell extracts, mucus, saliva, sputum, stool, physiological or cell secretions or other similar fluids. In one embodiment, the poly(amino acids) comprise the proteome of an animal cell, typically a mammalian cell. In another embodiment, the poly(amino acids) are derived from skin tissue, and are present in a latent fingerprint.

Depending on the source of the sample mixture, it optionally contains discrete biological ingredients other than the desired analytes, including poly(amino acids) other than those desired, amino acids, nucleic acids, carbohydrates, and lipids, which may or may not be removed in the course of, prior to, or after staining. In one aspect of the invention, the analytes in the sample mixture are separated from each other or from other ingredients in the sample mixture in the course of the method. In another aspect of the invention, the sample mixture thought to contain the analyte has undergone separation. In yet another aspect of the invention, the analytes are not separated. In one embodiment, the sample mixture is essentially cell-free. In another embodiment, the sample mixture comprises viable cells, non-viable cells, cellular organelles such as nuclei or mitochondria, or a mixture thereof. In another embodiment of the invention, the sample mixture comprises tissues, tissue slices, tissue smears, entire organs, or organisms.

The analytes are optionally unmodified, or have been treated with a reagent or molecular composition so as to enhance or decrease the mobility of the analytes in an electrophoretic gel. Such reagents may modify analytes by complexation, cleavage, changing the relative charge on the analyte, or by covalent coupling of a constituent. The presence or interaction of such a reagent in the sample mixture is detected by the change in electrophoretic mobility of the treated analytes, relative to untreated analytes having the same original composition, so that the distribution of the analytes indicates the presence of the modifying reagent.

The analytes are optionally further derivatized by inclusion of a radiolabel, or by covalent attachment to one or more additional fluorescent or chemiluminescent labels.

Typically the poly(amino acids) in the sample mixture have a molecular weight greater than about 500 daltons. More typically the poly(amino acids) are more than 800 daltons. The poly(amino acids) present optionally have essentially the same molecular weight or fall within a range of molecular weights. In one embodiment of the invention, the poly(amino acids) present are a mixture of poly(amino acids) of different molecular weights that are used as molecular weight standards. Typically, such a mixture contains equal mass quantities of myosin, β-galactosidase, phosphorylase B, bovine serum albumin, ovalbumin, carbonic anhydrase, trypsin inhibitor, lysozyme and aprotinin. The metal complexes of the present invention also stain low molecular weight peptides, polypeptides and proteins, such as insulin, aprotinin, or neuropeptides. The metal complexes of the invention may stain very small peptides, even peptides as small as a 15-mer or 7-mer. Staining of small peptides is typically enhanced where the peptide contains one or more basic amino acid residues.

In one embodiment of the invention, separated poly (amino acids) in electrophoretic gels are post-stained using the staining mixture, or are transferred to a filter membrane or blot or other solid or semi-solid matrix before being combined with the staining mixture. The present method is effective for both denaturing and non-denaturing gels. Denaturing gels optionally include a detergent such as SDS or other alkyl sulfonate (e.g. 0.05%–0.1% SDS). Typically, polyacrylamide or agarose gels are used for electrophoresis. Commonly used polyacrylamide gels include but are not limited to Tris-glycine, Tris-tricine, mini- or full-sized gels. Agarose gels include modified agaroses. Alternatively, the gel is an iso-electric focusing gel or strip. In addition to polyacrylamide and agarose gels, suitable electrophoresis gels are optionally prepared using other polymers, such as HYDROLINK Alternatively, the electrophoretic gel is a gradient gel. Useful electrophoretic gels for the present invention are either prepared according to standard procedures or are purchased commercially.

In another embodiment of the invention, the present method is used to detect poly(amino acids) present in a two-dimensional electrophoretic gel. In another embodiment of the invention, the electrophoretic gel is used for gel-mobility-shift analysis, where a polyacrylamide or agarose gel is cast and run in a buffer optimized to preserve the specific protein interaction of interest. In both embodiments, the staining mixture is optionally combined with the sample mixture at any stage in the electrophoresis procedure, but the dyes are preferably used following electrophoretic separation as a post-stain.

Many conventional protein electrophoresis gel staining techniques, such as ammoniacal silver staining, are unsuitable for pH-neutral gels, such as commercially available pre-cast gels that incorporate Tris-tricine and Tris-bicine, due to excessively high background staining. In contrast, the present method stains pH-neutral gels with high sensitivity. Even gels that incorporate a plastic backing, or that are prepared using a gel strengthening agent (such as DURACRYL or ACRYLAIDE) are stained effectively using the present method.

Where the sample mixture is an electrophoretic gel or a blot membrane, the poly(amino acids) of the sample mixture are typically present at a concentration of 1 ng/band–4 µg/band.

In yet another embodiment of the invention, the present method is used to detect poly(amino acids) that are themselves associated with a target of interest. For example, a target molecule is labeled with biotin, which is then labeled with streptavidin using standard immunological methods. The resulting target-biotin-streptavidin complex is then labeled using a europium stain of the present invention Luminescent detection of the target-biotin-streptavidin complex results in detection and/or localization of the target of interest. Similarly, a target can be labeled with a polypeptide, and the resulting increased concentration of poly(amino acid) is then directly detected using a metal complex of the invention. The use of time-resolved detection methods allows for sensitive detection of even small amounts of target.

Staining Mixture

In order to effect analyte staining, the sample mixture is combined with a staining mixture. A staining mixture is typically prepared by dissolving a selected europium complex in a solvent, such as water, DMSO, DMF or methanol, usually to a metal complex concentration of 0.1–250 µM, preferably 1–100 µM, more preferably approximately 50 µM. The complexes of the invention typically possess good aqueous solubility when they are substituted by multiple anionic or cationic moieties. These complexes usually do not require dissolution into organic solvents prior to preparing the aqueous solution. The concentrated stock solution is generally diluted with an aqueous solution according to the assay being performed. For staining analytes on gels or membranes, the metal complex is diluted into a solution that comprises water, and optionally further comprises additional formulation components, such as acids, buffering agents, inorganic salts, polar organic solvents, antioxidants, and ion chelators.

A particular metal complex is generally selected for a particular assay using one or more of the following criteria: sensitivity to the particular analyte under investigation, or to a specific class thereof, dynamic range, photostability, staining time, and insensitivity to the presence of undesired sample components. In one embodiment, the metal complexes of the present invention are capable of detecting 1–2 ng or less of poly(amino acid) per band in electrophoretic gels.

Selected metal complexes of the invention stain proteins at a wide variety of pH values. Typically the staining mixture has a pH of about 1 to about 7, more typically the staining mixture has a pH of about 4 to about 6. The pH of the staining mixture can be controlled by the selection of appropriate acidic components or buffering agents.

The pH of the staining mixture is optionally modified by the inclusion of a buffering agent in addition to or in place of an acidic component. In particular, the presence of a buffering agent has been shown to improve staining of electrophoretic gels, provided that an alcohol and an inorganic salt are included in the formulations as well. Any buffering agent that is compatible with the poly(amino acids) in the sample is suitable for inclusion in the staining mixture.

In one embodiment, the buffering agent is one of the so-called "Good's" buffers. "Good's" buffers include BES (N,N-bis[2-hydroxyethyl]-2-aminoethanesulfonic acid; 2-[bis(2-hydroxyethyl)amino]ethanesulfonic acid), BICINE (N,N-bis[2-hydroxyethyl]glycine), CAPS (3-[cyclohexylamino]-1-propanesulfonic acid), EPPS (N-[2-hydroxyethyl]piperazine-N'-[3-propanesulfonic acid]), HEPES ((N-[2-hydroxyethyl]piperazine-N'-[2-ethanesulfonic acid]), MES (2-[N-morpholino] ethanesulfonic acid), MOPS (3-[N-morpholino] propanesulfonic acid), PIPES (piperazine-N,N'-bis[2-ethanesulfonic acid]; 1,4-piperazinediethanesulfonic acid), TAPS (N-tris[hydroxymethyl]methyl-3-aminopropanesulfonic acid; ([2-hydroxy-1,1-bis (hydroxymethyl)ethyl]amino-1-propanesulfonic acid), TES (N-tris[hydroxymethyl]methyl-2-aminoethanesulfonic acid; 2-([2-hydroxy-1,1-bis(hydroxymethyl)ethyl]amino) ethanesulfonic acid), or TRICINE (N-tris[hydroxymethyl] methylglycine; N-[2-hydroxy-1,1-bis(hydroxymethyl)ethyl] glycine).

Other preferred buffering agents include salts of formate, citrate, acetate, N-(2-hydroxyethyl)-N'-(2-sulfoethyl) piperazine, imidazole, N-(2-hydroxyethylpiperazine)-N'-2-ethanesulfonic acid, Tris(hydroxymethyl)aminomethane acetate, or Tris(hydroxymethyl)aminomethane hydrochloride. In a preferred embodiment, the buffering agent is MES or sodium acetate. The buffering agent or mixture of buffering agents is typically present in the staining mixture at a concentration of 20 mM to 500 mM, preferably about 25 mM to about 100 mM.

Any inorganic salt that is adequately soluble in the formulation itself may be used in the staining formulations. Advantageous inorganic salts produce staining formulations that exhibit low background signals in stained gels. Typically, the inorganic salt dissolves to yield at least one ion having multiple charges, such as a magnesium salt. Particularly useful and inexpensive salts include ammonium sulfate, magnesium chloride, magnesium acetate, zinc chloride, magnesium sulfate and magnesium glucuronate present in the staining mixture at a concentration of 1–50%. In a preferred embodiment, the inorganic salt is ammonium sulfate or magnesium chloride, more preferably magnesium chloride. When present, magnesium chloride is typically present in the staining mixture at a concentration of about 4–45%, preferably about 5%–20%, more preferably about 6%–10%, and most preferably about 8%.

Inclusion of a polar organic solvent, typically an alcohol, in the staining mixture is recommended. Typically, the polar organic solvent is an alcohol having 1–6 carbons, or a diol or triol having 2–6 carbons. The polar organic solvent, when present, is typically included in the staining mixture at a concentration of 5–50%. The presence of a polar organic solvent is particularly advantageous when staining sodium dodecyl sulfate-coated proteins, as is typically the case when staining poly(amino acids) that have been electroblotted from SDS-polyacrylamide gels. Without wishing to be bound by theory, it appears that the presence of an alcohol improves luminescent staining of poly(amino acids) due to the removal of SDS from the protein. However, nitrocellulose membranes may be damaged by high concentrations of alcohol (for example, greater than about 20%), and so care should be taken to select solvent concentrations that do not damage the membranes present in the sample mixture.

Certain acid- and alcohol-containing formulations of Coomassie Blue dye cause irreversible acid-catalyzed esterification of glutamic acid side chain carboxyl groups of sample proteins, while formaldehyde, present in many silver staining formulations, leads to alkylation of $\alpha$- and $\epsilon$-amino groups. Such modifications hinder the subsequent identification of proteins by mass spectrometry by complicating the interpretation of spectra or by reducing peptide recovery. This undesirable modification of proteins by the staining mixture is prevented by selection of a less reactive alcohol for inclusion in the staining mixture. The use of low molecular weight diols and triols as the polar organic solvent results in several advantages for the instant method. First, the esterification of sample proteins is eliminated. Additionally, low molecular weight diols and triols are substantially less flammable than alcohols such as methanol and ethanol, resulting in staining mixtures that are safer to use in a laboratory setting. In one embodiment, the polar organic solvent is a diol or triol having 2–6 carbons. Preferably, the polar organic solvent is glycerol, glycolic acid, or a diol having 2–6 carbons. More preferably, the polar organic solvent is a diol that is 1,2-ethanediol or 1,2-propanediol. The polar organic solvent is typically present at a concentration of 5–50%. In one embodiment particularly preferred for staining isoelectric focusing gels, the polar organic solvent is a diol that is present at a concentration of 5–30%, preferably 5–15%. In another embodiment particularly preferred for staining SDS-polyacrylamide electrophoretic gels, the polar organic solvent is a diol that is present at a concentration of 30–40%, preferably 33–36%.

Staining of poly(amino acids) is optionally enhanced by the addition of an antioxidant or a metal ion chelator. Selected embodiments of antioxidants include glucuronic acid, ascorbic acid and citric acid. Selected embodiments of metal ion chelators include ethylenediamine diacetic acid, ethylenediamine tetraacetic acid (EDTA), ethylene glycol-bis-($\beta$-aminoethyl ether) tetraacetic acid (EGTA), citric acid, 1,2-bis-(2-aminophenoxyethane)-N,N,N',N'-tetraacetic acid (BAPTA), 2-carboxymethoxyaniline-N,N-diacetic acid (APTRA), and various crown ethers, cryptands and carcerands. Citric acid may act as both an antioxidant and a chelating group, and is a particularly preferred additive to the staining mixture.

Broadly speaking, two formulations of the staining mixture of the invention have been found to have highly effective poly(amino acid) staining properties. The first is similar to the staining formulation utilized for standard Coomassie Blue staining, and comprises 0 to 10% acid, such as acetic acid or formic acid, and 0 to 40% alcohol, such as methanol, ethanol, or diol having 2–6 carbons. This formulation is especially suitable for staining poly(amino acids) present on membranes, such as dot-blots, slot-blots, or electroblots, as well as staining of cells on tissue prints, with little background staining. The second preferred class of formulations is similar to those employed for colloidal Coomassie Blue staining of gels.

When the metal complexes of the invention are prepared in formulations similar to those utilized for colloidal Coomassie Blue staining, the staining mixture stains poly(amino acids) in polyacrylamide gels with greatly reduced background staining. A low background level of luminescence is particularly important for quantitative measurements of poly (amino acid) bands, as any destaining procedure would invariably remove some staining from the poly(amino acid) band as well.

Combined Mixture

The staining mixture is combined with the sample mixture in such a way as to facilitate contact between the metal complex and any analyte present in the combined mixture.

Destaining of stained gels is typically not necessary for luminescent detection of proteins using the metal complexes of the invention, although for certain staining formulations containing methanol/acetic acid, destaining typically improves poly(amino acid) detection in gels. For example, while staining of proteins in polyacrylamide gels is typically accompanied by some background staining of the gel matrix, such background staining can be reduced by incubation of the stained gel in a comparable formulation comprising an acid and an alcohol that does not contain the staining metal complex. This incubation typically removes dye from the gel background, with little loss of protein staining. Stained gels may also be washed briefly after staining to prevent transfer of the staining metal complex to other surfaces. The duration of staining is such that stained gels can be photographed months after staining without significant loss of signal.

Electrophoretic gels stained according to the method of the invention can subsequently be dried onto filter paper or between plastic sheets (e.g. cellophane), using standard procedures.

Where the staining method of the invention is being utilized to determine cell viability, the sample mixture is typically incubated with the staining mixture of the invention for about 5–10 minutes, preferably 5–6 minutes. Where the staining method of the invention is being utilized to stain tissue prints or cells on microscope slides, the sample mixture is typically incubated with the staining mixture of the invention for about 5–60 minutes, preferably for 10–30 minutes, more preferably for about 15 minutes.

Additional Reagents

The method of the present invention optionally further comprises one or more additional reagents that are simultaneously or sequentially combined with the sample mixture, the staining mixture, or the combined mixture. An additional reagent is optionally a detection reagent that colocalizes with the analyte in general or with specific poly(amino acids) to enhance the detection thereof by the method of the present invention. Alternatively, the additional reagent is useful for identification of other components in the sample mixture, such as an additional poly(amino acid) stain, nucleic acid stain, or a stain for lipids or carbohydrates. Or, the additional reagent is a detection reagent designed to interact with a specific portion of the sample mixture, so as to probe for a specific component of the sample mixture, where spatial coincidence of the metal complex and the detection reagent indicates that the additional reagent is also associated with the analyte.

The additional reagent also incorporates a means for producing a detectable response. A detectable response means a change in, or occurrence of, a parameter in a test system that is capable of being perceived, either by direct observation or instrumentally. Such detectable responses typically include the change in, or appearance of, color, fluorescence, reflectance, pH, chemiluminescence, infrared spectra, magnetic properties, radioactivity, light scattering, x-ray scattering, or the precipitation of an electron-rich product. Appropriate labels to provide a detectable response include, but are not limited to, a visible or fluorescent dye, a chemiluminescent reagent, an enzyme substrate that produces a visible or fluorescent precipitate upon enzyme action (for example, the action of horseradish peroxidase upon diaminobenzidine, or enzyme action on a labeled tyramide), visible- or fluorescent-labeled microparticles, a metal such as colloidal gold, or a silver-containing reagent, or a signal that is released by the action of light upon the reagent (e.g. a caged fluorophore that is activated by photolysis, or the action of light upon diaminobenzidine), or a radioactive signal. The detectable label of the additional reagent is detected simultaneously or sequentially with the optical signal of the complexes of the present invention.

In one embodiment of the invention, one or more additional metal complexes, including preferred embodiments described above, are the additional reagent(s). The individual metal complexes may be selected to exhibit overlapping spectral characteristics, such that energy transfer occurs between the complexes associated with the poly(amino acids), resulting in labeled poly(amino acids) that exhibit an extended Stokes shift. Alternatively, the additional dye(s) colocalize with the metal complex such that the labeling of some or all poly(amino acids) exhibits quenching. Alternatively, the additional reagent is another protein stain (such as CBB or silver stain) such that labeling of the poly(amino acids) is enhanced by the colocalization of staining.

Other useful additional reagents are fluorescent nucleic acid stains. A variety of appropriate nucleic acid stains are known in the art, including but not limited to, thiazole orange, ethidium homodimer, ethidium bromide, propidium iodide, Hoechst 33258, and DAPI. Additional useful nucleic acid stains are described in the international applications WO 93/06482, DIMERS OF UNSYMMETRICAL CYANINE DYES (published Apr. 1, 1993) or WO 94/24213, CYCLIC SUBSTITUTED UNSYMMETRICAL CYANINE DYES (published Oct. 27, 1994); U.S. Pat. No. 5,321,130 to Yue et al., 1994; or U.S. Pat. No. 5,410,030 DIMERS OF UNSYMMETRICAL CYANINE DYES CONTAINING PYRIDINIUM MOIETIES to Yue et al., 1995. The use of an appropriate nucleic acid stain in conjunction with the dyes of the present invention can be selected to permit simultaneous or sequential observation of poly(amino acids) and nucleic acids such as DNA and RNA.

In one embodiment, the additional reagent comprises a member of a specific binding pair having a detectable label. Representative specific binding pairs are shown in Table 3.

TABLE 3

| Representative specific binding pairs | |
|---|---|
| enzyme | enzyme substrate |
| antigen | antibody |
| biotin | avidin (or streptavidin) |
| IgG* | protein A or protein G |
| carbohydrate | lectin |
| nucleic acid aptamer | protein |

*IgG is an immunoglobulin

The additional reagent may be used in conjunction with enzyme conjugates to localize the detectable response of the reagent. Enzyme-mediated techniques take advantage of the attraction between specific binding pairs to detect a variety of analytes. In general, an enzyme-mediated technique uses an enzyme attached to one member of a specific binding pair or series of specific binding pairs as a reagent to detect the complementary member of the pair or series of pairs. In the simplest case, only the members of one specific binding pair are used. One member of the specific binding pair is the analyte, i.e. the substance of analytical interest. An enzyme is attached to the other (complementary) member of the pair, forming a complementary conjugate. Alternatively, multiple specific binding pairs may be sequentially linked to the analyte, the complementary conjugate, or to both, resulting in a series of specific binding pairs interposed between the analyte and the detectable enzyme of the complementary conjugate incorporated in the specific binding complex.

In another embodiment of the invention, a protein electrophoresis gel stained according to the method of the invention may be electroblotted to a filter membrane. After blocking non-specific binding sites, the blot is incubated with a detection reagent that is a primary antibody. The resulting immunolabeled blot is then restained according to the method of the invention. The metal complex of the invention will associate with and stain the primary antibody just as it stains other poly(amino acids), and thereby increase the overall staining of the electroblot. In this embodiment, even an unlabeled antibody could be used for immunolabeling, as the presence of the label does not appreciably affect staining by the instant complexes. The use of antibodies derivatized with amine-rich tags (such as polyhistidine) results in enhanced staining by the instant complexes. This methodology is particularly useful for high-throughput image analysis, where automated workstations can rapidly screen stained blots for spots that increase in intensity upon labeling and restaining. The staining of other poly(amino acid) labels, for example actin that is used to identify actin-binding proteins, is readily accomplished in the same manner.

As an example of an application of an additional detection reagent, a significant problem in two-dimensional gel electrophoresis is the alignment of a target protein detected using antibody-based or lectin-based methods with the entire constellation of species resolved by 2-D electrophoresis. Known protein stains, such as Amido Black and CBB staining, are difficult to destain, prevent subsequent immunostaining, and are generally difficult to use in this application The staining method of the instant invention permits facile luminescent two-color detection in 2-D electrophoresis gels. As an example, 2-(5'-chloro-2- phosphoryloxyphenyl)-6-chloro-4(3H)-quinazolinone (U.S. Pat. No. 5,316,906 to Haugland et al. (1994)) produces a photostable, fluorescent yellow-green precipitate that is spectrally complementary to the europium complexes of the invention. The use of alkaline phosphatase-conjugated antibodies to detect target proteins in conjunction with Compound 1, for example, permits two color visualization of proteins in a single gel or electroblot. The appropriate selection of emission filters allows spectral separation of signal from the target protein and the total protein profile. It is possible to select fluorophores for the detection of specific classes of proteins, such as glycoproteins, lipoproteins or phosphoproteins that are spectrally well suited for use in combination with the metal complexes of the invention.

Illumination and Observation

The metal complex is most typically detected by its intrinsic luminescence. After addition of the metal complex to the sample mixture, the sample mixture is illuminated by a light source capable of exciting the stained sample mixture. Typically, the sample mixture is excited by a light source capable of producing light at or near a wavelength of peak absorption of the metal complex, such as an ultraviolet or visible wavelength emission lamp, an arc lamp. Typically, ultraviolet excitation of the metal complex occurs at 250–370 nm. Preferably the sample mixture is excited with a wavelength within 20 nm of the maximum absorption of the metal complex. Although excitation by a source more appropriate to the maximum absorption band of the metal complex may result in higher sensitivity, the equipment commonly available for excitation of fluorescent samples can be used to excite the stains of the present invention. Selected equipment that is useful for illuminating the metal complex includes, but is not limited to, ultraviolet transilluminators, ultraviolet epi-illuminators, hand-held ultraviolet lamps, mercury arc lamps, and xenon lamps. These illumination sources are optionally integrated into laser scanners, fluorescence microplate readers, standard or mini fluorometers, microscopes, flow cytometers, gel readers, or chromatographic detectors.

As the metal complexes of the invention possess long-lifetime luminescence, observation of luminescence occurs at greater than ~100 nanoseconds after illumination, even up to greater than 10 microseconds after illumination. Utilizing this 'time-resolved' luminescence results in the exclusion of almost all of the sources of background fluorescence, which is typically short-lived. This property is particularly useful where the sample, or an additional detection reagent present in the sample, is intrinsically fluorescent, or has fluorescent impurities.

Preferably, the metal complexes of the present invention possess an absorption maximum between 250–370 nm in the ultraviolet region. More preferably, the metal complexes of the present invention are selected such that the absorption maximum of the metal complex matches the wavelength of a laser illumination source. Preferably, the complexes of the present invention excite efficiently in the ultraviolet wavelength range, more preferably at or near 300 nm, 365 nm, and/or 254 nm.

The detectable optical response of the metal complex in response to illumination is detected qualitatively, or optionally quantitatively. The detectable optical response of the metal complex is typically a long-lifetime luminescence response.

The optical response is typically detected by means that include visual inspection, CCD cameras, video cameras, photographic film, or the use of currently used instrumentation such as laser scanning devices, fluorometers, photodiodes, quantum counters, epifluorescence microscopes, scanning microscopes, flow cytometers, fluorescence microplate readers, or by means for amplifying the signal such as photomultiplier tubes. When recording the optical response of electrophoretic gels, the use of a film such as POLAROID film results in enhanced sensitivity of signal versus purely visual observation. The metal complex of the invention typically has an emission near 615 nm, although selection of an appropriate nitrogen donor ligand can be used to modify both the absorption and emission wavelengths somewhat. The sensitivity of detection is improved by use of techniques that permit separation of the poly(amino acids) on very thin gels or in microtube capillaries. The detection limits may also be improved if the medium is illuminated by a stronger light such as a laser, detected with a more sensitive detector, or background signals are reduced via detection of delayed luminescence. The high Stokes shifts of the metal complexes of the present invention result in an excellent signal-to-noise ratio by decreasing the contribution of scattered light and endogenous fluorescence to the background.

The presence of luminescence is optionally used to identify the presence of the analyte in the test sample. Alternatively, the detectable optical response is quantified and used to measure the concentration of the analyte in the test sample mixture. Quantification is typically performed by comparison of the optical response to a prepared standard or to a calibration curve. Typically, the measured optical response is compared with that obtained from a standard dilution of a known concentration of the analyte or analyte mixture in an electrophoretic gel, or on a membrane. Generally a standard curve must be prepared whenever an accurate measurement is desired. Alternatively, the standard curve is generated by comparison with a reference dye or dyed particle that has been standardized versus the metal complex-stained analyte.

In one aspect of the invention, stained electrophoretic gels are used to analyze the composition of complex sample mixtures and additionally to determine the relative amount of a particular poly(amino acid) in such mixtures. Stained gels are also used to estimate the purity of isolated proteins and to determine the degree of proteolytic degradation of poly(amino acids) in the sample mixture. In addition, electrophoretic mobility is optionally used to provide a measure of the size of uncharacterized poly(amino acids) and to analyze subunit composition for multi-subunit proteins, as well as to determine the stoichiometry for subunits bound in such proteins. In the case of isoelectric focusing electrophoresis (IEF), electrophoretic mobility is used to provide a measure of the net molecular charge possessed by the poly(amino acid).

The use of the complexes of the invention provides higher sensitivity poly(amino acid) detection than other comparable electrophoresis gel stains. In one aspect of the invention, the instant method is utilized with automated electrophoresis methods. Using the instant method, the bright luminescence of even small amounts of poly(amino acids) permits their detection by automated imaging systems. Further, unlike many electrophoretic gel stains, the instant method incorporates 'endpoint staining'. That is, while an electrophoretic gel may be compromised by silver staining beyond the optimum end point, gels stained using the instant method do not suffer from prolonged staining, and in some formulations do not require destaining, further simplifying the use of automated staining systems. The sensitivity and bright luminescence of the instant metal complexes facilitate the accurate localization of poly(amino acid) bands or spots by automatic systems, permitting their subsequent transfer and/or analysis.

In one aspect of the invention, the localization of poly(amino acid) bands or spots further comprises the physical removal of the bands or spots, followed by separation of the poly(amino acids) from the electrophoretic matrix. In another aspect of the invention, the localization of poly(amino acid) bands or spots further comprises ionization of the poly(amino acids) and characterization by mass spectroscopy, or transfer and subsequent analysis of the poly(amino acids) by Edman sequencing.

The instant metal complexes have utility as a single color viability stain when used in conjunction with flow cytometry or luminescence imaging. While not wishing to be bound by theory, it appears that nonviable cells (having compromised cell membranes) offer greater accessibility of the amines present in cellular proteins to the metal complex, resulting in enhanced luminescence relative to stained viable cells.

Due to the simplicity of use of the instant metal complexes, they are particularly useful in the formulation of a kit for the labeling of poly(amino acids), comprising one or more metal complexes (preferably in a stock solution), instructions for the use of the metal complex to stain or detect poly(amino acids), and optionally comprising poly(amino acid) standards and other components (such as buffers or wash solutions). In one embodiment, the kit of the invention comprises an aqueous stock solution of a metal complex of the invention and one or more additional kit components.

The additional kit components optionally include acids, buffering agents, inorganic salts, polar solvents, antioxidants, or metal chelators. The additional kit components are present as pure compositions, or as aqueous solutions that incorporate one or more additional kit components. Any or all of the kit components optionally further comprise buffers. Where the kit component is an acid, it is optionally phosphoric acid, acetic acid, or trichloroacetic acid. Where the additional kit component is a polar solvent, it is typically a lower alcohol such as methanol or ethanol, or a diol having 2–6 carbons. Where the additional kit component is an inorganic salt, it is typically an ammonium or magnesium salt.

The examples below are given so as to illustrate the practice of this invention. They are not intended to limit or define the entire scope of this invention.

EXAMPLES

Example 1

Synthesis of Compound 1

Figure 2:
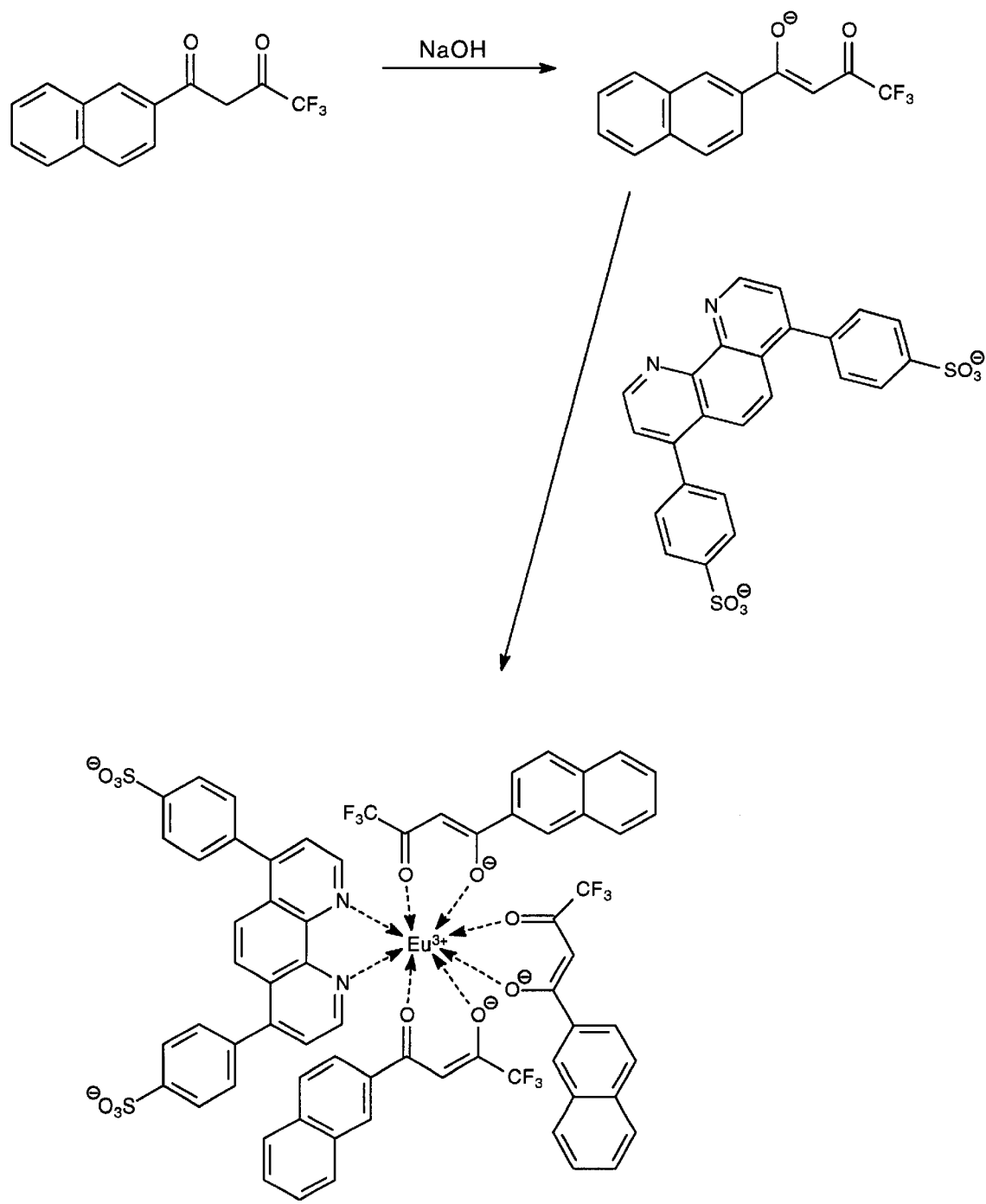
FIG. 2. The synthesis of Compound 1, as described in Example 1.

A diagram of the synthesis of Compound 1 is provided in FIG. 2.

4-Naphthyl-1,1,1-trifluoro-2,4butanedione (3.1 mmol) and bathophenanthroline disulfonic acid (1 mmol) are dissolved in methanol (30 mL). To the solution is added 1 M NaOH (3.1 mL) dropwise, and the resulting mixture is stirred at room temperature for 2 hours. To the mixture is slowly added $EuCl_3$ (1 mmol in 15 mL water), and the resulting solution is stirred for 4 hours. The resulting reaction mixture is heated at 50° C. until the blue-fluorescent bipyridine ligand is completely converted into the bright red-fuorescent complex. The reaction mixture is cooled to room temperature, and left in a refrigerator overnight. The formed precipitate is collected by filtration, and washed with isopropyl alcohol. The crude product is further purified by recrystallization from water-isopropyl alcohol. The colorless complex emits bright red fluorescence with maximum absorption near 360 nm and maximum emission near 620 nm.

By selection of appropriate nitrogen donor ligands and acetylacetonate ligands, a broad variety of individual europium complexes may be prepared using this general synthetic method, according to methods known in the art.

Example 2

Visualization of Proteins Dot-blotted or Slot-blotted to Nitrocellulose Membrane A serial dilution of the protein of interest is prepared in distilled and deionized water (dd-$H_2O$) or other suitable solution such as 7% acetic acid or 20 mM Tris HCl, pH 6.8, 500 mM NaCl. For dot-blotting, 1–5 µL volumes of the protein sample are applied to a 0.4 µm pore size nitrocellulose membrane using a pipetter. Slot-blotting is performed using a Bio-Dot SF vacuum apparatus (Bio-Rad Laboratories, Hercules, Calif.). For slot-blotting, membranes are rehydrated with 100 µL/well dd-$H_2O$ samples are applied to the membranes (200 µL/well), wells are rinsed twice with 600 µL of 100 mM formic acid, 100 mM NaCl, pH 3.7 and twice with 600 µL of dd-$H_2O$. Following dot- or slot-blotting, membranes are allowed to air dry to minimize loss of protein during subsequent staining steps. The membrane is incubated for 5 minutes each in four changes of dd-$H_2O$. The membrane is completely immersed in 25 mM MES buffer, pH 6.0, 10% propylene glycol, 150 µM Compound 1. The membrane is washed 4–6 times for 1 minute each in dd-$H_2O$. This serves to remove excess dye from the membrane. The membrane is allowed to air dry and is subsequently viewed using a reflective 302 or 365 nm UV light source. Spotted proteins appear as red to orange luminescent bands on a faint pink to faint blue background. By comparison, staining proteins on nitrocellulose membranes with Coomassie blue dye by standard methods requires lengthy destaining of the membrane in 7% acetic acid/10% methanol for adequate visualization of proteins.

Example 3

Visualization of Protein Electroblotted to Nitrocellulose Membrane

Proteins of interest are separated by SDS-polyacrylamide gel electrophoresis and transferred to nitrocellulose membrane using standard procedures. The membrane is allowed to air dry and is stained in 25 mM sodium acetate, pH 4.0, 10% propylene glycol, 150 µM Compound 1 as described in Example 2 for slot-blotted proteins. The membrane is allowed to air dry and is subsequently viewed using a reflective 302 or 365 nm UV light source. This procedure is also appropriate for poly(vinylidene difluoride) membrane as long as the dry membranes is rehydrated with methanol or other suitable organic solvent prior to electroblotting and staining. Proteins appear as red to orange luminescent bands on a very faint pink background. Compared with other staining procedures for electroblotted proteins, Compound 1 has several advantages in terms of sensitivity and compatibility with immunoblotting.

TABLE 4

Comparison of different stains for the detection of electroblotted proteins.

| Stain | Sensitivity[1] (ng/band) | Membranes stained | Reversibility[2] | Compatible with immuno-blotting?[3] | Compatible with Edman sequencing?[4] | Compatible with mass spectrometry?[5] |
|---|---|---|---|---|---|---|
| Colloidal gold | 2–4 | PVDF, nitrocellulose | No | No | No | No |
| Compound 1 | 2–8 | PVDF, nitrocellulose | Yes | Yes | Yes | Yes |
| India Ink | 4–8 | PVDF, nitrocellulose | No | No | No | No |
| Coomassie Brilliant Blue R-250 | 10–30 | PVDF | No | No | Yes | Yes |
| Eu(BPDS)$_3^{3-}$ | 15–30 | PVDF, nitrocellulose | Yes | Yes | Yes | Yes |
| Colloidal silver | 15–30 | PVDF, nitrocellulose | No | not determined | not determined | Yes |
| Amido Black | 15–60 | PVDF, nitrocellulose | No | No | Yes | Yes |
| Ferrozine/ferrous | 15–100 | PVDF, nitrocellulose | Yes | Yes | Yes | Yes |
| Fast Green FC | 15–100 | PVDF, nitrocellulose | No | No | Yes | Yes |
| Congo Red | 30–60 | PVDF, nitrocellulose | No | not determined | not determined | not determined |
| Ponceau S | 60–100 | nitrocellulose | Yes | Yes | Yes | Yes |

[1]Note that typically only 50–70% of the protein applied to a polyacrylamide gel is subsequently transferred to the blotting membrane. Sensitivity values are given in terms of actual amount of protein loaded on the gel prior to electrotransfer.
[2]By reversible is meant that staining is removed by a change in pH or inclusion of an organic solvent such as methanol.
[3]Staining does not interfere with subsequent immunoblotting techniques well-known in the art
[4]Staining does not interfere with subsequent characterization by Edman degradation using techniques well-known in the art
[5]Staining does not interfere with subsequent characterization by mass spectronietry using techniques well-known in the art

Example 4

Detection of Proteins in Filtration Plates by Standard or Time-resolved Luminescence Prior to protein application the hydrophobic membranes in individual wells of a 96-well Millipore MultiScreen filtration plate are wetted with methanol and then rinsed with 7% acetic acid using a vacuum manifold per manufacturer's instructions (Millipore Corporation, Bedford, Mass.). 0.2 to 1000 ng/mm² of bovine serum albumin is applied to individual wells without application of a vacuum. The plate is incubated for 30–60 minutes before the protein is removed by application of a vacuum. The filtration plate is then allowed to air dry and then wetted with methanol or similar organic solvent. Wells are next incubated in 200 µL of 7% acetic acid, 10% methanol, 100 micromolar Compound 1 for 15–30 minutes. The dye solution is removed from the wells by pipetting and 200 µL of 7% acetic acid is applied and removed by pipetter 3–4 times to remove any unbound dye. The filtration plate is subsequently read using a Perkin-Elmer HTS 7000 microplate reader or similar device. An excitation filter of 365 nm and an emission filter of 615 nm is selected. Measurements are made through the top face of the plate. Gain is set to 60 and 10 flashes are used per well. Integration time is set to 20 lseconds. For time-resolved luminescence, all instrument parameters are maintained, except that integration of the signal begins approximately 10 µsecond after a flash of light and the integration time is increased to 100 µseconds. Instrument software provides digital values corresponding to the luminescence intensity of the signal from the dye in each well.

Example 5

Visualization of Proteins Resolved by Sodium Dodecylsulfate Polyacrylamide Gel Electrophoresis (with Destaining)

Proteins of interest are separated by SDS-polyacrylamide gel electrophoresis utilizing a 4% T, 2.6% C stacking gel, pH 6.8 and 15% T, 2.6% C separating gel, pH 8.8 according to standard procedures. The gel is subsequently incubated in 25% trichloroacetic acid for 20 minutes, incubated in three changes of 30% methanol for 20 minutes each, and stained in 30% methanol, 1.5 µL Compound 1 for 1–2 hours. Inspection of the gel using a hand-held long-range UV light source indicates that the entire gel is stained. The gel is subsequently transferred to a destaining solution of 30% methanol, 7% acetic acid and is incubated for an additional 4–6 hours. At this point dye is eluted from the polyacrylamide matrix but selectively retained on the proteins within the matrix. The gel is viewed using a 302 or 365 nm UV transilluminator. Proteins appear as red to orange luminescent bands on a pale pink background.

Example 6

Visualization of Proteins Resolved by Sodium Dodecylsulfate Polyacrylamide Gel Electrophoresis (without Destaining)

Proteins of interest are separated by SDS-polyacrylamide gel electrophoresis utilizing a 4% T, 2.6% C stacking gel (% T=percentage of total monomers (including crosslinker) in a polyacrylamide gel; % C=percentage of crosslinker in a polyacrylamide gel), pH 6.8 and 15% T, 2.6% C separating gel, pH 8.8 according to standard procedures. After electrophoresis, gels are incubated in 8% magnesium chloride, 34% propylene glycol, 100 mM sodium acetate, pH 4.0, 1.5 µM Compound 1 for 2–15 hours. Gels are rinsed in 10% methanol, 7% acetic acid for 10–15 minutes and viewed using a 302 or 365 nm UV transilluminator. Proteins appear as red to orange luminescent bands on a clear background. This is the preferred method of staining polyacrylamide gels as any destaining step also removes dye from proteins, thus reducing the signal.

TABLE 5

| Detection Reagent | Sensitivity (ng/band) |
| --- | --- |
| Colloidal Coomassie Blue dye | 8–16 |
| Silver stain | 2–4 |
| SYPRO ® Orange dye | 2–4 |
| Compound 1 | 1–2 |

Example 7
Detection of Proteins on Membranes or in Gels using a CCD Camera Scanner Proteins on membranes or in polyacrylamide gels are stained as described in Examples 2–6. Stained material is placed in a CCD camera-based imaging workstation such as a Bio-Rad Fluor-S Max Multi-Imager system (Bio-Rad, Hercules, Calif.). The cited unit provides excitation epi-illumination of about 302 nm. A 520 nm long pass emission filter is used with the Fluor-S. Images of gels are captured utilizing standard software-driven procedures provided by the manufacturer. Proteins appear as white bands on a gray to black background or as black bands on a light gray to white background on the computer monitor, depending upon the display mode selected. Instrument software provides digital values corresponding to the fluorescence intensity of the signal in each band.

Example 8
Visualization of Amino Acid Homo- and Hetero-polymers on Nitrocellulose Membrane Homopolymers of poly-L-arginine, asparagine, histidine, lysine, aspartate, glutamate, alanine, glycine, isoleucine, leucine, methionine, serine, threonine, tryptophan, tyrosine and proline are prepared at a concentration of 1 μg/mL. The amino acid heteropolymers, poly(glutamate, alanine, tyrosine), poly(glutamate, tyrosine), poly(lysine, tyrosine), poly(glutamate, lysine, tyrosine), and poly(arginine, tyrosine) are prepared in an identical manner as the homopolymers. All polymers are obtained from Sigma Chemical Company (St. Louis, Mo.). 1–5 μL volumes of the polymers are applied to a nitrocellulose membrane and allowed to air dry. Staining is performed according to Example 2, using a dye of the invention. Only select polymers are noted to stain with the dye, as demonstrated by strong orange to red luminescence. The dye is observed to interact primarily with polymers containing the basic amino acids; histidine, lysine or arginine. Weak interaction with tryptophan- and tyrosine-containing polymers is also observed.

Example 9
Edman Sequencing of Proteins Electroblotted to Transfer Membranes

Proteins of interest are subjected to electrophoresis, subsequently transferred to poly (vinylidene difluoride) membranes and stained as described in Example 3. After the target proteins are identified, the bands are excised with a sharp razor. The excised bands are then either used directly or incubated in 150 mM Tris, pH 8.8, 20% methanol for 30 minutes and rinsed in 3 changes of deionized water. The Tris/methanol incubation destains the proteins, thus removing excess dye. For internal protein sequencing, the target proteins are excised from the nitrocellulose membrane, subjected to in situ proteolytic cleavage for 3 hours at 37° C., and in the presence of 10% acetonitrile, 3% Tween-80 in 100 mM ammonium bicarbonate, pH 8.3. Resulting fragments are then separated by micro-bore reverse phase HPLC. Selected peak fractions are analyzed by automated Edman degradation. Proteins subjected to this protocol produce high quality spectra with excellent initial and repetitive sequencing yields.

Example 10
Matrix-assisted Laser Desorption Mass Spectrometry-based

Proteins of interest are subjected to electrophoresis, subsequently transferred to poly(vinylidene difluoride) membranes and stained as described in Example 3. After target proteins are identified, the bands are excised with a sharp razor. The selected bands are then washed 3 times 5 minutes in 25 mM ammonium bicarbonate pH 7.8, 10% methanol and allowed to dry. After drying, the bands are cut into 1–2 mm squares and incubated in 20 μg/ml trypsin in digest buffer (25 mM ammonium bicarbonate, pH 7.8 with 1% octyl β-glucoside and 10% methanol added). Sufficient volume of the trypsin digestion mixture is added to cover the membrane squares. Proteins are digested at room temperature for 5–6 hours and then incubated overnight at 27–28 ° C. The peptides are extracted with formic acid:ethanol, (1:1) and then lyophilized. After lyophilization, the peptides are resuspended in water for analysis by matrix assisted laser desorption ionization mass spectrometry (MALDI-MS). Equal volumes of the peptide digests are mixed with α-cyano-4-hydroxycinnamic acid matrix (10 mg/mL in 70% acetonitrile/$H_2O$). The mixture is spotted onto the sample plate and air dried prior to analysis. MALDI-MS analysis is performed using a Voyager Mass Spectrometer, (PerSeptive BioSystems, Framingham, Mass., USA). The instrument is calibrated with Substance-P (1347.7 Da) and insulin (5731.4 Da). The peptide masses obtained from the trypsinized protein are used to search the EMBL peptide database. Proteins are readily identified with good peptide sequence coverage.

Example 11
Staining Fixed Mammalian Cells

ROS 17.1 osteosarcoma cells (American Type Culture Collection (ATCC), Manassas, Va.) are grown on glass cover slips and fixed in 3.7% formaldehyde in 100 mM Tris-base, 150 mM NaCl, pH 7.5 by standard procedures. Fixed cells are rinsed 3 times in 2.7 mM KCl, 1.5 mM $KH_2PO_4$, 136 mM NaCl, 8.1 mM $Na_2HPO_4$, pH 7.0 (phosphate-buffered saline). Cover slips are incubated in 50 μM Compound 1, 7% acetic acid for 10 minutes and then washed twice with dd-$H_2O$ . Cells are viewed with a Nikon Fluorescence microscope using a UV excitation filter and 635 +/−28 nm emission filter. Cells appear as red to orange fluorescence regions on a dark background.

Example 12
Visualization of Tissue Prints

The tips of green onion shoots are cut as close to the end as possible to expose the meristematic region. The cut ends of the plant are pressed lightly against the nitrocellulose surface of a Grace Bio-Labs Oncyte™ film slide for 15 to 120 seconds (Grace BioLabs, Bend, Oreg.). The slide is allowed to air dry for one hour and the slide is fixed in 3.7% paraformaldehyde in TBS (100 mM Tris-base, 150 mM NaCl, pH 7.5) using a humidified chamber. The slide is washed three times for 15 minutes each in TBS and then twice more with dd-H$_2$O. The slide is stained for 15 minutes in 50 μM Compound 1, 7% acetic acid in a humidified chamber. The slide is subsequently washed twice in dd-H$_2$O. Tissue prints are viewed on a standard 300 nm UV light box. Tissue is easily visualized as red to orange fluorescence regions on a dark background.

Example 13
Visualization of Latent Fingerprints on Solid Substrata

A thumb or finger is firmly pressed against a dry glass microscope slide, nitrocellulose or poly(vinylidene difluoride) membrane (substrata). The substrata is incubated in 100 mM sodium acetate, pH 4.0, 100 μM Compound 1 for 15–30 minutes. The substrata is incubated in dd-H$_2$O for 5 minutes and allowed to air dry. The substrata is viewed with a hand held UVM-57 midrange UV-302 nm lamp (UVP, Inc. Upland, Calif.). Fingerprints appear as red to orange fluorescent patterns on a very faint pink background.

Example 14
Detection of DNA on Nitrocellulose Membranes

A dilution series of calf thymus DNA (Sigma Chemical Company, St. Louis, Mo.) is prepared and applied to nitrocellulose membranes by slot blotting. Slot-blotting is performed using a Bio-Dot SF vacuum apparatus (Bio-Rad Laboratories, Hercules, Calif.) according to the manufacturer's instructions. The apparatus is assembled and full vacuum applied to facilitate tightening of the screws. In sequence, using the gentle vacuum setting, membranes are rehydrated with 100 μl/well of distilled and deionized water (dd-H$_2$O), samples are applied to the membranes (200 μg/well) in 100 mM formic acid, 100 mM NaCl, pH 3.7 and wells are rinsed twice with 400 μl 100 mM formic acid, 100 mM NaCl. pH 3.7 and twice with 400 μl of dd-H$_2$O. Following blotting, membranes are allowed to air dry and DNA bands are fixed to the membrane by irradiation with a UV transilluminator. Blots are incubated for 1 hour in 10% propylene glycol, 100 mM MES, pH 6.0, 75 μM Compound 4. Subsequently, blots are illuminated with a hand held 300 nm UV illuminator to visualize DNA bands. Bands appear as pink to orange bands on a pale pink to blue background. DNA is readily detected in amounts ranging from 1 to 250 ng/mm$^2$.

It is to be understood that, while the foregoing invention has been described in detail by way of illustration and example, numerous modifications, substitutions, and alterations are possible without departing from the spirit and scope of the invention as described in the following claims.

What is claimed is:

1. A method of detecting an analyte that is a polymer or macromolecule that incorporates primary, secondary, or tertiary amines, comprising the steps of:
   a) combining a sample mixture that is thought to contain the analyte with a staining mixture that contains one or more europium complexes to form a combined mixture;
   wherein each europium complex independently comprises:
      i) a europium (III) ion;
      ii) at least one polydentate nitrogen donor ligand; and
      iii) at least one acetylacetonate ligand;
   b) incubating the combined mixture for a time sufficient for the europium complexes in the staining mixture to associate with the analyte in the sample mixture to form a stained analyte complex that gives a detectable luminescence response upon illumination;
   c) illuminating said stained analyte complex; and
   d) observing said luminescence response.

2. A method, as claimed in claim 1, wherein each europium complex has an overall anionic charge.

3. A method, as claimed in claim 1, wherein the analyte is a poly(amino acid).

4. A method, as claimed in claim 1, wherein each polydentate nitrogen donor ligand independently has the formula

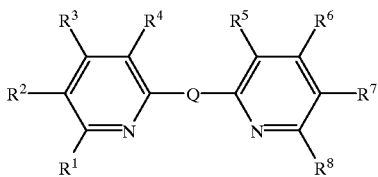

wherein substituents $R^1$, $R^2$, $R^3$, $R^4$, $R^5$, $R^6$, $R^7$, and $R^8$ are independently selected from hydrogen, halogen; CN; alkyl, perfluoroalkyl, or alkoxy, each having 1–6 carbon atoms; carboxy; carboxyalkyl, carboxyalkoxy, carboxyalkylamino, or carboxylalkylthio, each having 2–7 carbons; amino, salt of amino, alkylamino, or dialkylamino, where each alkyl group has 1–6 carbons; aryl; heteroaryl; or any two adjacent substituents $R^1$, $R^2$, $R^3$, $R^4$, $R^5$, $R^6$, $R^7$, and $R^8$ taken in combination form an additional fused aromatic ring that is optionally substituted by halogen; sulfonic acid or salt of sulfonic acid; cyano; alkyl, perfluoroalkyl, or alkoxy, each having 1–6 carbons; amino; alkylamino having 1–6 carbons; dialkylamino having 2–12 carbons; carboxy; or carboxyalkyl, carboxyalkoxy, carboxyalkylamino, or carboxyalkylthio, each having 2–7 carbons; and Q is a single covalent bond; or Q is a formal single bond, and $R^4$ and $R^5$ when taken in combination are —$CR^9$=$CR^{10}$—; or Q is —$(CR^{11}{}_2)_a$—$X_b$—$(CR^{12}{}_2)_c$—, where a, b and c are each 0 or 1, provided that when b=1, a+c must equal 0 or 2; or Q is a 2,6-disubstituted pyridyl;
   wherein $R^9$ and $R^{10}$ are independently H; alkyl, perfluoroalkyl, or alkoxy having 1–6 carbon atoms; a sulfonic acid, a salt of sulfonic acid; an amino, alkylamino or dialkylamino, where each alkyl group has 1–6 carbons; a carboxy; or carboxyalkyl, carboxyalkoxy, carboxyalkylamino or carboxyalkylthio having 2–7 carbons; an aryl or heteroaryl; halogen; or CN;
   $R^{11}$ and $R^{12}$ are independently H or alkyl having 1–6 carbon atoms;

X is optionally O, S, $NR^{13}$, or —$CR^{14}R^{15}$—;
   where $R^{13}$ is H, $C_1$–$C_6$ alkyl, or phenyl that is optionally further substituted one or more times in any combination by alkyl, perfluoroalkyl, or alkoxy having 1–6 carbon atoms; sulfonic acid, salt of sulfonic acid; $NO_2$; amino, alkylamino or dialkylamino, where each alkyl group has 1–6 carbons; carboxy; carboxyalkyl, carboxyalkoxy, carboxyalkylamino or carboxyalkylthio having 2–7 carbons; halogen, or CN; and
   $R^{14}$ and $R^{15}$ are independently H, alkyl having 1–6 carbons, sulfonic acid or salt of sulfonic acid; and
said 2,6-disubstituted pyridyl is optionally further substituted by alkyl, perfluoroalkyl, or alkoxy having 1–6 carbon atoms; sulfonic acid, salt of sulfonic acid; amino, alkylamino or dialkylamino, where each alkyl group has 1–6 carbons; carboxy; or carboxyalkyl, carboxyalkoxy, carboxyalkylamino, or carboxyalkylthio having 2–7 carbons; or halogen.

5. A method, as claimed in claim 4, wherein said polydentate nitrogen donor ligand has the formula

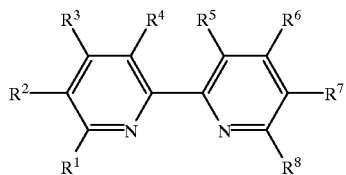

where $R^1$–$R^8$ are as defined previously.

6. A method, as claimed in claim 4, wherein said polydentate nitrogen donor ligand has the formula

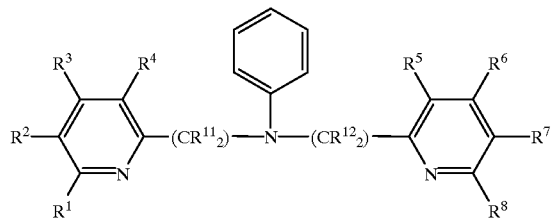

wherein $R^1$–$R^8$, $R^{11}$ and $R^{12}$ are as defined previously.

7. A method, as claimed in claim 4, wherein said polydentate nitrogen donor ligand has the formula

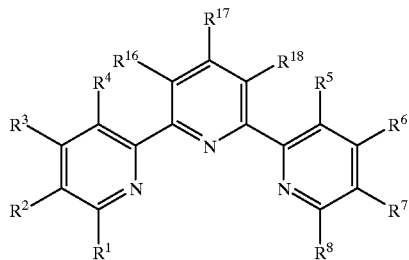

where
 $R^1$–$R^4$ and $R^5$–$R^8$ are as defined previously; and
 $R^{16}$, $R^{17}$, and $R^{18}$ are independently H; alkyl, perfluoroalkyl, or alkoxy having 1–6 carbon atoms; sulfonic acid, salt of suffonic acid; amino, alkylamino or dialkylamino, where each alkyl group has 1–6 carbons; carboxy; or carboxyalkyl, carboxyalkoxy, carboxyalkylamnino, or carboxyalkylthio having 2–7 carbons; halogen, or CN.

8. A method, as claimed in claim 4, wherein said nitrogen donor ligand has the formula

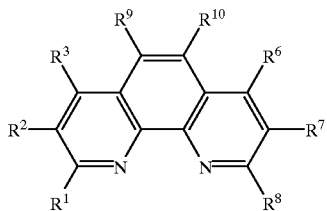

where $R^1$–$R^3$, $R^6$–$R^8$, $R^9$ and $R^{10}$ are as defined previously.

9. A method, as claimed in claim 8, wherein $R^3$ and $R^6$ are each phenyl that is optionally and independently substituted by sulfonate.

10. A method, as claimed in claim 1, wherein each of said acetylacetonate ligands independently has the formula

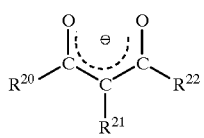

wherein
 $R^{20}$ is alkene, alkyne, alkoxide, ether, thioether, carboxy, carboxyalkyl, carboxyalkoxy, carboxyalkylamino, or carboxylalkylthio, each having 2–7 carbons; amino, or salt of amino, or $R^{20}$ is alkyl having 1–6 carbons that is optionally and independently substituted one or more times by halogen, cyano, nitro, sulfonate, amino, salt of amino, substituted or unsubstituted aryl or heteroaryl; or $R^{20}$ is an alkyl having 1 carbon that is substituted by an electron withdrawing group EWG;
 $R^{21}$ is H, halogen, cyano, nitro, sulfonate, amino, salt of amino, substituted or unsubstituted aryl or heteroaryl, alkene, alkne, alkoxide, ether, thioether, carboxy; or carboxyalkyl, carboxyalkoxy, carboxyalkylamino, or carboxylalkylthio, each having 2–7 carbons; or amino, or salt of amino; or $R^{21}$ is an electron withdrawing group EWG;
 $R^{22}$ is a substituted or unsubstituted aryl or heteroaryl.

11. A method, as claimed in claim 10, wherein either $R^{21}$ is an EWG, or $R^{20}$ is a $C_1$-alkyl that is substituted by an EWG.

12. A method, as claimed in claim 10, wherein
 $R^{20}$ is a perfluorinated alkyl having 1–6 carbons;
 $R^{21}$ is H;
 $R^{22}$ is a substituted or unsubstituted phenyl, naphthyl, or thienyl that is optionally substituted by one or more anionic moieties or cationic moieties.

13. A method, as claimed in claim 12, wherein said each acetylacetonate ligand has the formula

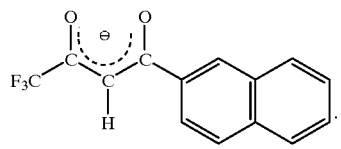

14. A method, as claimed in claim 1, further comprising quantitating said analyte by measuring said detectable luminescence response and comparing said measurement with a standard.

15. A method, as claimed in claim 3, wherein said analyte is present on or in a solid or semi-solid matrix.

16. A method, as claimed in claim 15, wherein said matrix is an electrophoretic gel or a membrane.

17. A method, as claimed in claim 3, further comprising electrophoretically separating the sample mixture before or while it is combined with the staining mixture.

18. A method, as claimed in claim 17, wherein the electrophoretic separation, the illuminating step, or the observing step is accomplished by automated methods.

19. A method, as claimed in claim 3, further comprising analyzing the poly(amino acid) by mass spectroscopy.

20. A method, as claimed in claim 3, further comprising analyzing the poly(amino acid) by Edman sequencing.

21. A method, as claimed in claim 1, further comprising adding an additional reagent to the sample mixture, the staining mixture, or the combined mixture.

22. A method, as claimed in claim 1, wherein said complex comprises a europium (III) ion, exactly one bidentate nitrogen donor ligand, and at least three acetylacetonate ligands.

23. A method, as claimed in claim 22, wherein each nitrogen donor ligand has the formula

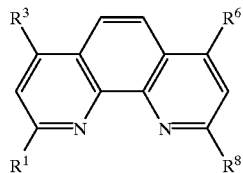

wherein $R^1$ and $R^8$ are independently H or carboxylic acid;

$R^3$ and $R^6$ are independently H, phenyl, or sulfophenyl; and and each acetylacetonate ligand has the formula

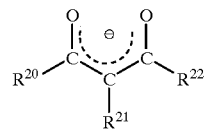

wherein $R^{20}$ is $CF_3$; $R^{21}$ is H; and $R^{22}$ is thienyl, or $R^{22}$ is naphthyl that is optionally substituted by sulfonate.

24. A method, as claimed in claim 1, wherein said observing step occurs at least 100 nsec after said illuminating step.

25. A method, as claimed in claim 1, wherein said observing step occurs at least 10 μsec after said illuminating step.

* * * * *